(12) United States Patent
Nevo et al.

(10) Patent No.: US 8,044,190 B2
(45) Date of Patent: Oct. 25, 2011

(54) STRESS TOLERANT ORGANISMS EXPRESSING A MAP KINASE HOMOLOGUE

(75) Inventors: Eviatar Nevo, Haifa (IL); Yan Jin, Haifa (IL); Weining Song, Haifa (IL)

(73) Assignee: Carmel-Haifa University Economic Corp. Ltd., Haifa (IL)

( * ) Notice: Subject to any disclaimer, the term of this patent is extended or adjusted under 35 U.S.C. 154(b) by 730 days.

(21) Appl. No.: 11/662,360

(22) PCT Filed: Sep. 8, 2005

(86) PCT No.: PCT/IL2005/000953
§ 371 (c)(1),
(2), (4) Date: May 23, 2008

(87) PCT Pub. No.: WO2006/027779
PCT Pub. Date: Mar. 16, 2006

(65) Prior Publication Data
US 2008/0263729 A1    Oct. 23, 2008

Related U.S. Application Data

(60) Provisional application No. 60/607,573, filed on Sep. 8, 2004.

(51) Int. Cl.
| | | |
|---|---|---|
| C12N 15/31 | (2006.01) | |
| C12N 15/70 | (2006.01) | |
| C12N 15/80 | (2006.01) | |
| C12N 15/82 | (2006.01) | |
| C12N 1/00 | (2006.01) | |
| C12N 5/04 | (2006.01) | |
| A01H 5/00 | (2006.01) | |

(52) U.S. Cl. .................. 536/23.74; 435/320.1; 435/419; 435/254.11; 435/252.3; 800/298

(58) Field of Classification Search .................. None
See application file for complete search history.

(56) References Cited

U.S. PATENT DOCUMENTS 5,859,337 A    1/1999  Gasser et al.

FOREIGN PATENT DOCUMENTS

WO          03097827 A1    11/2003

OTHER PUBLICATIONS

Kültz D. et al. Evolution of osmotic stress signaling via MAP kinase cascades. J Exp Biol. Nov. 1998;201(Pt 22):3015-21. Review.*
Kis-Papo T. et al. Spatiotemporal diversity of filamentous fungi in the hypersaline Dead Sea. Mycol. Res. vol. 105, Issue 6, pp. 749-756 (Jun. 2001).*
Prabhala G. et al. Architectural features of pre-mRNA introns in the fission yeast *Schizosaccharomyces pombe*. Yeast. Mar. 1992;8(3):171-82.*
Brewster J.L. et al. An osmosensing signal transduction pathway in yeast. Science. Mar. 19, 1993;259(5102):1760-3.*
Turk,M. et al., "The HOG Pathway in the Halophilic Black Yeast Hortaea werneckii: Isolation of the HOG1 Homolog Gene and Activation of HwHog1p", FEMS Microbiology Letters, 216:193-199 (2002).
Database UniProt 'Online!, "Mitogen-activated Protein Kinase HOGA", EBI Accession No. Uniprot:Q5H7P1, Database Accession No. Q5H7P1, May 10, 2005.
Database UniProt Online!, "Probable Osmotic Sensitivity Map Kinase", EBI Accession No. Uniprot:Q8TFX5, Database Accession No. Q8TFX5, Jun. 1, 2002.
Database UniProt 'Online!, "Hog1p-like Protein", EBI Accession No. Uniprot:Q8NJT7, Database Accession No. Q8NJT7, Oct. 1, 2002.
Akhtar N. et al "Osmoregulation and protein expression in a pbs2Δ mutant of *Saccharomyces cerevisiae* during adaptation to hypersaline stress" FEBS Letters vol. 403 Issue 2. pp. 173-180 (1997).
Albertyn et al; "GPD1, which encodes glycerol-3-phosphate dehydrogenase, is essential for growth under osmotic stress in *Saccharomyces cerevisiae*, and its expression is regulated by the high-osmolarity glycerol response pathway" Molecular and Cellular Biology, vol. 14 No. 6, p. 4135-4144 (1994).
Deglos J. et al; "Activation and regulation of the Spc1 stress-activated protein kinase in *Schizosaccharomyces pombe*" Molecular and Cellular Biology, vol. 16, No. 6, p. 2870-2877 (1996).
Hayashi H et al; "Transformation of *Arabidopsis thaliana* with the codA gene for choline oxidase; accumulation of glycinebetaine and enhanced tolerance to salt and cold stress" The Plant Journal 12(1), 133-142 (1997).
Heribert Hirt; "Multiple roles of MAP kinases in plant signal transduction" Trends in Plant Science vol. 2, Issue 1, pp. 11-15 (1997).
Norbeck J. et al; "Purification and Characterization of Two Isoenzymes of DL-Glycerol-3-phosphatase from *Saccharomyces cerevisiae*" The Journal of Biological Chemistry vol. 271, No. 23, Issue of Jun. 7, pp. 13875-13881 (1996).
Norbeck J. et al; "Metabolic and Regulatory Changes Associated with Growth of *Saccharomyces cerevisiae* in 1.4 M NaCl" The Journal of Biological Chemistry vol. 272, No. 9, Issue of Feb. 28, pp. 5544-5554 (1997).
Popping B. et al; "The *Pisum sativum* MAP kinase homologue (PsMAPK) rescues the *Saccharomyces cerevisiae* hog1 deletion mutant under conditions of high osmotic stress" Plant Molecular Biology 31: 355-363, (1996).

* cited by examiner

*Primary Examiner* — Cynthia Collins
(74) *Attorney, Agent, or Firm* — Browdy and Neimark, PLLC

(57) ABSTRACT

The present invention provides a MAP kinase homologue gene, designated EhHOG, isolated from *Eurotium herbariorum*, a common fungal species from the extreme hypersaline environment of the Dead Sea, capable of improving tolerance of plants and other organisms to abiotic stresses such as osmotic, heat, dehydration, freezing-thawing, oxidative and salinity stress.

16 Claims, 6 Drawing Sheets

```
SpSTY1    ---MAEFIRTQIFGTCFEITTRYSDLQPIGMGAFGLVCSAKDQLTGMNVAVKKIMKPFST  57
ScHog1    MTTNEEFIGTQIFGTVFEITNRYNDLNPVGMGAFGLVCSATDTLTSQPVAIKKIMKPFST  60
AnSakA    ---MAEFVRAQIFGTTFEITSRYTDLQPVGMGAFGLVCSARDQLTAQPVAVKKIMKPFST  57
EhHOG     ---MAEFVRATIFGTTFEITSRYTELQPVGMGAFGLVCAARDQLTGAPVAVKKIMKPFST  57
AnMpkC    ---MAEFIRSDILGTTFETTSRYANLQPVGLGTAGVVCSAYDLISEQVVAIKKMMKPFHS  57
             **:  *:** ** *.** :*:*;*;*;  *;**:* *  ::    **;**;****  :

SpSTY1    PVLAKRTYRELKLLKHLRHENIISLSDIFISPFEDIYFVTELLGTDLHRLLTSRPLETQF 117
ScHog1    AVLAKRTYRELKLLKHLRHENLICLQDIFLSPLEDIYFVTELQGTDLHRLLQTRPLEKQF 120
AnSakA    PVLSKRTYRELKLLKHLRHENIISLSDIFISPLEDIYFVTELLGTDLHRLISSRPLEKQF 117
EhHOG     PVLSKRTYRELKLLKHLGHENIICLSDIFISPLEDIYSVTELLGTDLHRLLTSRPLEKQF 117
AnMpkC    TSVAKRTYREVKLLRHLRHDNLINMSDIFISPLEDVYLVTELLGTDLHRLLNGKPLESKF 117
          .  ::******:***:** *:*;* :.***:**:**:* **** *******;  ;***.:*

SpSTY1    IQYFLYQILRGLKFVHSAGVIHRDLKPSNILINENCDLKICDFGLARIQDPQMTGYVSTR 177
ScHog1    VQYFLYQILRGLKYVHSAGVIHRDLKPSNILINENCDLKICDFGLARIQDPQMTGYVSTR 180
AnSakA    IQYFLYQIMRGLKYVHSAGVVHRDLKPSNILINENCDLKICDFGLARIQDPQMTGYVSTR 177
EhHOG     IQYFLYQILRGLKYVHSAGVVHRDLKPSNILINENCDLKICGFGLARVQDPQMTGYVSTR 177
AnMpkC    AQYFTYQILRGLKYIHSAGVIHRDLKPGNLLINENCDLKICDFGLARVQEPQMTGYVSTR 177
           *** ***:****;:*****:*******.*;:*********.****:*;.**********

SpSTY1    YYRAPEIMLTWQKYNVEVDIWSAGCIFAEMIEGKPLFPGRDHVNQFSIITELLGTPPMEV 237
ScHog1    YYRAPEIMLTWQKYDVEVDIWSAGCIFAEMIEGKPLFPGKDHVHQFSIITDLLGSPPKDV 240
AnSakA    YYRAPEIMLTWQKYDAKVDVWSAACIFAEMLLGAPLFPGKDHVNQFSIITELLGTPPDDV 237
EhHOG     YYRAPEIMLTWQKYDVEVDIWSAGCIFAEMLDGKPLFPGKDHVNQFSIITELLGTPPDDV 237
AnMpkC    YYRAPEIMLTWQRYGSKVDLWSVGCILAEMLLGRPLFPGTDHINQFWLITDLLGNPPDEV 237
          ************:*. ;**:** ..**;**;    *  ***** **;;**  :**;***.** ;*

SpSTY1    IETICSKNTLRFVQSLPQKEKVPFAEK-------FKNADPDA-------IDLLEKMLVFD 283
ScHog1    INTICSENTLKFVTSLPHRDPIPFSER-------FKTVEPDA-------VDLLEKMLVFD 286
AnSakA    IQTICSENTLRFVKSLPKREPQDLAKLPKFLALVHPDKKPEEDEDYKNTINLLKAMLVYN 297
EhHOG     IETICSENTLRFVKSLPKRERQPLTSR-------FKNADPEA-------VDLLERMLVFD 283
AnMpkC    IDRITTNNVRNPAPDLQPSNHLEPANG-------NRRIDSSG------ALNLLDNLLVFD 284
          *:  * ::*.  .. ,*      :    :.                     ::**. :**::

SpSTY1    PRKRISAADALAHNYLAPYHDPTDEPVADEVFDWSFQDNDLPVETWKVMMY----SEVLS 339
ScHog1    PKKRITAADALAHPYSAPYHDPTDEPVADAKFDWHFNDADLPVDTWRVMMY----SEILD 342
AnSakA    PKDRISAEAALAAPYLAPYHDETDEPVAEEKFDWSFNDADLPVDTWKIMMY----SEILD 353
EhHOG     PKKRIRAGEALAHEYLAPYHDPTDEPAQEKFDWSFNDADLPVDTWRIMMY----SEILD 339
AnMpkC    PDRRISAEQGLMHPWMAPYHDPTDEPVATEQFDWSFNDADLPLDTWKIMMYVHHCSDVVS 344
          *  ** *   .*    ;   *****  ****   *   *** *;* ***;;**;;***      *;::.

SpSTY1    FHNMD------------------------------------------------------ 344
ScHog1    FHKIGGSDGQIDISATFDDQVAAATAAAAQAQAQAQAQVQLNMAAHSHNGAGTTGNDHSD 402
AnSakA    FHNIDQGG--------------------------------------------------- 361
EhHOG     FHNIDQSE--------------------------------------------------- 347
AnMpkC    FTL-------------------------------------------------------- 347
          *   .

SpSTY1    -----------------------NELQS---- 349
ScHog1    IAGGNKVSDHVAANDTITDYGNQAIQYANEFQQ---- 435
AnSakA    --------------------DINPALVEGAGLNQQGFQ- 379
EhHOG     --------------------DAGQVLVEGVGDGQQAFAA 366
AnMpkC    ---------------------------------
                                         .  ..
```

Fig. 1A

STRESS TOLERANT ORGANISMS EXPRESSING A MAP KINASE HOMOLOGUE

FIELD OF THE INVENTION

The present invention relates to a MAP kinase homologue gene, designated EhHOG, isolated from *Eurotium herbariorum*, a common fungal species from the extreme hypersaline environment of the Dead Sea, to vectors comprising it, and to transgenic plants and other organisms containing said gene. In particular, it relates to methods for conferring salt tolerance and other generalized stresses tolerance such as heat tolerance, oxidative tolerance osmotic tolerance and freezing-thawing tolerance on plants and other organisms.

BACKGROUND OF THE INVENTION

The productivity of crops is greatly affected by salt stress. The progressive salinization of soil, estimated at around 20% of irrigated land, has made the genetic improvement of salt tolerance an urgent priority for the future of agriculture. Salt tolerant plants can facilitate use of marginal areas for crop production, or allow a wider range of sources of irrigation water.

The Dead Sea is one of the most saline lakes on earth (salinity about 340 g/l). The pioneering studies of Benjamin Elazari-Volcani in the 1930s on the biology of the Dead Sea revealed a variety of microorganisms, including red halophilic Archaea, unicellular green algae (*Dunaliella parva* Lerche), different types of bacteria, and possibly even protozoa (Volcani, 1944). Recently, filamentous fungi were isolated from surface water to 300 m depths down in Dead Sea (Buchalo et al., 1998; Nevo et al., 2003). The fungi isolated from the Dead Sea did not grow in undiluted Dead Sea samples. But these isolated fungi showed a remarkable salt tolerance and, in many cases, even had a requirement for high salt concentrations, making them halophilic. *Eurotium herbariorum* is the most common species isolated from Dead Sea water from the surface to 300 m in all investigated seasons (Kis-Papo et al., 2001). All these organisms needed to adapt to the extremely high salinity of the Dead Sea brines.

Exposure to high environmental osmolarity leads to dehydration in mammals; thus, consequently, cell viability decreases. To cope with this, the cells of both prokaryotic and eukaryotic microorganisms have developed mechanisms to adapt to severe osmotic changes in their environments, which is often called osmoregulation. To adapt to salt stress, microorganisms balance high external osmotic pressure by synthesizing and/or accumulating low-molecular mass compounds which are compatible with cellular function and do not inhibit the enzymes. Increased synthesis and/or accumulation of glycerol and other compatible solutes, mainly polyols, have been observed to be the major feature of fungi osmoregulation (Mager and Varella, 1993).

Eukaryotic organisms use different MAN kinase (MAPK) cascades to regulate various aspects of cellular function (Banuett, 1998; Gustin et al., 1998). MAPKs that specifically transmit environmental stress signals are also known as stress activated protein kinases. This pathway is called the high osmolarity glycerol (HOG) response pathway in *Saccharomyces cerevisiae* (Brewster et al., 1993). Members of this MAPK subfamily include Hog1 in *S. cerevisiae*, Spc1 (also called Sty1) in *Schizosaccharomyces pombe*, SakA in *Aspergillus nidulans*, and p38/JNK in the mammalian. Indeed, *S. cerevisiae* hog1 mutants are sensitive to high osmolarity, whereas spc1 mutations in *S. pombe* result in sensitivity to high osmolarity, heat shock, and oxidative stress. Activation of the HOG pathway increases the transcription of some proteins, including enzymes involved in glycerol synthesis (Albertyn et al., 1994; Norbeck et al., 1996). As a result, a high accumulation of glycerol inside the cell occurs and leads to increased internal osmolarity and restores the osmotic gradient between the cells and their environment (Akhtar et al., 1997; Norbeck & Blomberg, 1997). Therefore, HOG1 gene holds a key position in osmoadaptation of the yeast *S. cerevisiae*.

The presence of HOG1 homologous genes has been reported in fungal species (Degols et al., 1996), plants (Hirt, 1997), and animals (Marshall, 1994) indicating that this pathway is conserved among eukaryotes. However, no information is available in osmosensing signal transduction pathway in *E. herbariorum*.

In the past few years there have been large advancements in the identification of genes that are responsible for salt tolerance in halophytic plants. Today salt tolerant tomatoes have been produced using genes identified from *Arabidopsis thaliana* and *Saccharomyces cerivisiae*. Serrano and coworkers have identified two genes, HAL1 (Gaxiola et al., 1992) and HAL2 (Glaser et al., 1993) in *Saccharomyces cerivisiae* by selecting for genes whose overexpression leads to improved growth on saline conditions. A HAL1 homolog is present in plants, where it is induced by NaCl and abscisic acid, a plant hormone known to mediate adaptation of plants to osmotic stress (Murguia et al., 1995).

Another gene, calcineurin, or phosphoprotein phosphatase type 2B (PP2B), is a calmodulin-regulated enzyme found in many organisms, including yeast. Although its physiological functions are not well understood, it is known that yeast strains which do not contain active calcineurin proteins are more sensitive to growth inhibition by salt than are wild-type strains. Bacterial genes associated with salt tolerance have also been identified (Tarczynski et al., 1993).

The genetic manipulation of crop species with individual transgenes could lead to an improvement in tolerance level, which would be sufficient from a breeding point of view. Some transgenes, related mainly to the synthesis of osmolytes, have been introduced in tobacco (Traczynski et al., 1993) and *Arabidopsis* (Hayashi et al., 1997). In general, the expression of those transgenes seems to confer a low tolerance level to osmotic (water deficit) and/or salt (NaCl) stress. U.S. Pat. No. 5,859,337 describes isolation of two genes from *Arabidopsis* coding for STZ and STO polypeptides, capable of conferring salt tolerance to plants and other organisms. PCT Publication WO 03/097827 discloses salt-tolerant tomato plants comprising betaine aldehyde dehydrogenase (BADH) gene.

Despite the efforts toward cloning genes conferring tolerance to high saline condition, no single salt tolerance gene has been isolated from the Dead Sea microorganisms. The present invention addresses these needs.

SUMMARY OF THE INVENTION

The present invention relates to a MAP kinase homologue gene isolated from *Eurotium herbariorum*, herein designated EhHOG, the coding region of said EhHOG gene being represented by SEQ ID NO:1 herein, and to an isolated DNA having a nucleotide sequence differing from SEQ. ID NO: 1 in codon sequence due to the degeneracy of the genetic code. The gene EhHOG codes for the EhHOG protein of SEQ ID NO: 2.

The present invention further relates to plants and other organisms transformed with said EhHOG gene and expressing the EhHOG protein of SEQ ID NO: 2, which confers tolerance to abiotic stresses such as osmotic, high salinity, heat, freeze, dehydration, or oxidative stress.

BRIEF DESCRIPTION OF THE FIGURES

FIGS. 1A-1B show that the EhHOG gene encodes a member of the stress MAPK family. 1A. Multiple alignment (CLUSTAL W software) of homologous protein from *E. herbariorum*, EhHOG (SEQ ID NO:2); *A. nidulans*, SakA (An-Saka, SEQ ID NO:15) (AF282891); *A. nidulans*, Mpkc (An-MpkC, SEQ ID NO:16) (AF195773); *S. pombe*, STY1 (SpSTY1, SEQ ID NO:13) (X89262) and *S. cerevisiae*, Hog1 (ScHog1, SEQ ID NO:14) (U53878), is shown. Conserved TGY phosphorylation lip found in stress MAP kinases is shaded. Boxed amino acid represents the C-terminal common docking (CD) motif, in which the conserved hydrophobic amino acids tyrosine (Y) and histidine (H) are underlined, and conserved acidic aspartic acids (D) are bold. *=perfectly conserved residues; :=very similar residues; .=similar residues. 1B. Rooted phylogenetic tree of MAPK family constructed by the neighbor-joining method (45) based on amino acid sequences by the program MEGA 2.1. The numbers at nodes are bootstrap confidence values based on 1,000 replicaes. The tree was corrected with Poisson correction. Accession numbers of used genes were listed in the supplementary table. P38, animal SAPK2 CLUSTER; JNK (c-jun N-terminal protein kinase), animal SAPK1 cluster; HOG, fungi SAPK cluster; PERK, plant ERK cluster; ERK1 and ERK5, human and animal ERK cluster; YERK1 and YERK2, yeast ERK1 and ERK2 clusters. The conserved dual phosphorylation motif TXY (threonine-variable amino acid-tyrosine) of each subfamily is shown in parentheses.

DETAILED DESCRIPTION OF THE INVENTION

Figure 1B:
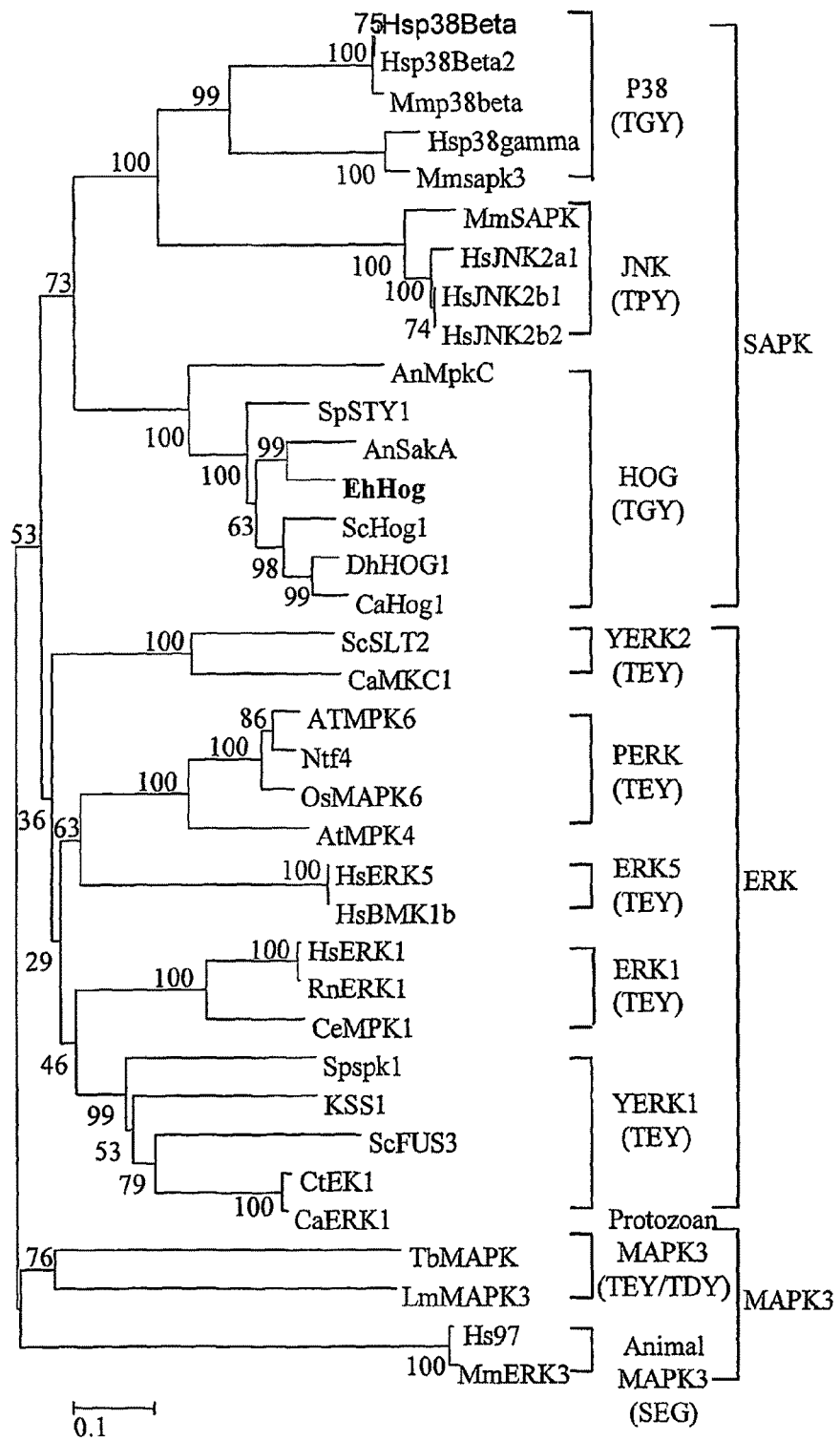

In one aspect, the present invention relates to an isolated gene comprising a DNA having a nucleotide sequence selected from the group consisting of SEQ ID NO: 1 and isolated DNA having a nucleotide sequence differing from SEQ ID NO: 1 in codon sequence due to the degeneracy of the genetic code.

The DNA of SEQ ID NO: 1 corresponds to the coding region of the EhHOG gene, isolated from *Eurotium herbariorum*, found in the Dead Sea, Israel. This gene codes for the EhHOG protein of the amino acid sequence shown in SEQ ID NO: 2.

The present invention further relates to a chimeric gene construct capable of expression in plant cells and in other microorganisms, like yeasts, comprising: (a) a DNA sequence of SEQ ID NO: 1 coding for the EhHOG protein of SEQ ID NO: 2, and (b) DNA sequences enabling expression of the EhHOG protein in the host cells. In one embodiment, one of the DNA sequences that enable the expression of the EhHOG protein in the host cell is a promoter. Such promoter may be a constitutive promoter, a stress-induced promoter, a tissue-specific promoter and any other promoter known in the art that enables the expression of the EhHOG protein in the host cell.

The invention further relates to a recombinant vector carrying the gene comprising a DNA having a nucleotide sequence consisting of SEQ ID NO: 1, in particular a recombinant expression vector comprising a chimeric gene construct in which the DNA of SEQ ID NO: 1 is operably linked to DNA sequences enabling expression of the EhHOG protein in host cells such as plant cells, yeasts or other microorganisms.

The vector used to introduce the nucleic acid into the host cell may be a plasmid, in which the DNA encoding the EhHOG protein is inserted into a unique restriction endonuclease cleavage site. The DNA is inserted into the vector using standard cloning procedures readily known in the art. This generally involves the use of restriction enzymes and DNA ligases, as described, for example, by Sambrook et al. (1989). The resulting plasmid, which includes nucleic acid encoding the EhHOG protein, can then be used to transform a plant cell (see generally, Gelvin and Schilperoort, 1994), or to transform another host cell.

For the transformation, the plasmid preferably also includes a selectable marker. Commonly used selectable markers include the kanamycin-resistance, kanamycin phosphotransferase II (nptII) gene, the hygromycin-resistance, hygromycin phosphotransferase (hpt) gene, the phosphinothricin acetyl transferase gene (bar), the 5-enolpyruvylshikimate-3-phosphate synthase (EPSPS), neomycin 3'-O-phosphotransferase (npt II), or acetolactate synthase (ALS). In preferred embodiments of the invention, the selectable marker is the hpt or nptII gene that allows selection of the transformants with hygromycin or kanamycin, respectively.

The plasmid may also include a reporter gene that, upon expression, provides a clear indication that genetic transformation did take place. Commonly used reporter genes are beta-glucuronidase (GUS), luciferase and green fluorescent protein (GFP). Reporter genes are often placed downstream of the promoter region and in the proximity of the gene of interest to ensure that they are expressed together and not separated by crossover events.

The plasmid preferably also includes suitable promoters for expression of the nucleic acid encoding the EhHOG protein and for expression of the selectable marker gene. In one embodiment, for the transformation of plants, the promoter is a constitutive promoter, for example, the cauliflower mosaic virus 35S (35S CaMV) promoter, commonly used for plant transformation, as well as the rice actin 1 (Act1), the Ubiquitin 1 (Ubi1), the alpha-amylase gene promoter, and promoters of genes induced by stress. In other embodiments, the promoter may be a tissue-specific promoter or the endogenous promoter of the EhHOG gene. In one preferred embodiment, the promoter used in the present invention is the 35S CaMV promoter. In the plasmid, the nucleic acid encoding the EhHOG protein may be under the control of one promoter and the marker gene may be under control of the same or of a different promoter.

In a further embodiment, the present invention provides host cells, e.g., plant cells carrying the nucleic acid of SEQ ID NO:1 encoding the EhHOG protein. In another embodiment, the present invention provides transgenic plants carrying the nucleic acid of SEQ ID NO: 1 encoding the EhHOG protein.

For plant transformation, the plasmid also preferably includes a nucleic acid molecule encoding a 3' terminator such as that from the 3' non-coding region of genes encoding a proteinase inhibitor, actin, or nopaline synthase (NOS). In a preferred embodiment, the plasmid of the present invention includes the nopaline synthase (NOS) terminator.

In one embodiment of the invention, the plasmid includes an enhancer element or elements that enhance the transcription of the EhHOG gene.

The plasmid is preferably a binary vector in which the genes of interest are inserted within the T-DNA borders. Examples of such vectors that can be used in the present invention are vectors obtainable from commercial sources such as the pCambia 1301, the pBI121, which contains a low-copy RK2 origin of replication, the neomycin phosphotransferase (nptII) marker gene with a nopaline synthase (NOS) promoter and a NOS 3' polyadenylation signal, the pBI101 and functionally similar vectors described by Becker et al. (1992), and the pPZPY112 vector.

For the transformation of the plants, any suitable method can be used such as *Agrobacterium*-mediated transformation or particle bombardment (also known as biolistic transformation).

In the *Agrobacterium*-mediated transformation, plant cells are contacted with an inoculum of the bacteria transformed with the plasmid comprising the gene that encodes for the EhHOG protein of the invention, for example by inoculating the plant cells with a suspension of the transformed bacteria. Suitable bacteria from the genus *Agrobacterium* that can be utilized to transform plant cells include the species *Agrobacterium rhizogenes* and *Agrobacterium tumefaciens*, preferably *A. tumefaciens* strains LBA4404 or EHA105. *Agrobacterium* spp. are transformed with the plasmid by conventional methods well-known in the art.

Using the floral dip transformation protocol (Clough et al., 1998), the *A. tumefaciens* strain carrying the EhHOG gene in the binary vector is grown in a growth medium in the presence of antibiotic, e.g. kanamycin, to select for the binary plasmid. The bacteria are spun down and resuspended in a 5% sucrose solution, followed by the addition of a surfactant, e.g. Silwet L-77. After mixing, the plants (after flowering) are dipped into the bacteria solution and kept under a dome or cover for 16-24 hours. The seeds are recovered and putative transformants are selected by plating the sterilized seeds on an antibiotic, e.g. hygromycin, and transplanting the putative transformants to soil. For higher rates of transformation, plants may be dipped two or three times at seven day intervals.

In cereals, the most commonly used tissue for transformation of wheat and barley has been the immature embryo from the developing grain (Weeks et al., 1993; Nehra et al., 1994; Becker et al., 1994; Wan and Lemaux, 1994; Barcelo and Lazzeri, 1995).

For the transformation of cereal plants, direct insertion of the DNA of interest may be carried out using the particle bombardment (biolistics) technique. According to this approach, rapidly propelled tungsten or gold microprojectiles (which are smaller than the plant cells) coated with the DNA of interest are blasted into cells. After the target tissue is bombarded with the DNA-coated particles under vacuum, the DNA of interest disperses from the particles within the cells and then integrates into their genome (Harwood et al., 2000). In an alternative, the particle bombardment technique can be combined with the *Agrobacterium* technique to facilitate transformation (Tingay et al., 1997; Cheng et al., 1997)

The invention further relates to a transgenic plant transformed with the DNA of SEQ ID NO: 1, that encodes the protein EhHOG consisting of the amino acid sequence as shown in SEQ ID NO: 2, said DNA being operably linked to DNA sequences enabling expression of the EhHOG protein in plant cells and subsequent improvement of tolerance of the plant to abiotic stresses such as osmotic, heat, freeze, dehydration, oxidative or high salinity stresses. Thus, the invention includes a transgenic plant which contains in its cells a chimeric gene construct capable of expression in plant cells, comprising: (a) a DNA sequence of SEQ ID NO: 1 coding for the EhHOG protein of SEQ ID NO: 2, and (b) DNA sequences enabling expression of the EhHOG protein in plant cells.

The transgenic plant of the invention may also contain an enhancer element or elements that enhances the transcription of the SEQ ID NO: 1, independent of orientation of the enhancer or its distance from the gene promoter.

The transgenic plants according to the invention include, without being limited to, edible crop species such as tomatoes, beans, including soybeans, and peas, and cereals such as wheat, barley, corn, rice, oats, and forage and turf grasses.

In another embodiment, the invention relates to a host cell, e.g., a microorganism, preferably yeast, cell comprising the DNA sequence of SEQ ID NO:1 coding for the EhHOG protein. In another embodiment, the invention relates to a biologically pure culture of a microorganism, preferably yeast, comprising the DNA of SEQ ID NO: 1 that encodes the protein EhHOG consisting of the amino acid sequence as shown in SEQ ID NO: 2, said DNA being operably linked to DNA sequences enabling expression of the EhHOG protein in the microorganism cells and subsequent improvement of tolerance of the microorganism to abiotic stresses, such as osmotic, heat, freeze, dehydration, oxidative or particularly, high salinity, stresses.

For the transformation of yeasts, mainly of the species *S. cerevisiae* or *Schizosaccharomyces pombe*, it is usual to use plasmids capable of autonomous replication in the yeast cell by the presence of a replication origin recognized by the replication machinery of the host cell. These plasmids generally comprise the replication origin of the 2-micron plasmid present in most of this species, or even as ARS segment of autonomous replication of chromosomal origin. As a marker gene, there is generally used a gene which codes for an enzyme involved in the biosynthesis of an essential metabolite, e.g., an amino acid. In such a case, the host cell to be used is a yeast strain, which, through mutation, has become auxotrophic for this metabolite. By inoculating with this strain a medium free from said metabolite, only those cells transformed by a plasmid bearing the missing gene will be able to grow.

These plasmids often further comprise bacterial sequences capable of ensuring their replication and their selection in an intermediate bacterial host, e.g., *Escherichia coli*. Finally, to ensure an expression level as high as possible of the coding part of interest, it is necessary to associate it with an efficient promoter. Various strong promoters are known in yeast, e.g., the promoters of alcohol dehydrogenase (ADH), 3-phosphoglycerate kinase (PGK) and galactose (GAL).

The carbohydrates which can be utilized by the yeast strains of the present invention include any of the starch or sugar containing materials normally fermented to form ethanol or carbon dioxide, including for example, grapes. The fermentations are normally run under the usual fermentation conditions. The fermentation product may then be further treated to produce a beverage such as bear or wine. The yeast strains may be also used as a leaving agent in baked goods.

The invention further encompasses the transformation of other microorganisms, e.g. genetically modified microorganisms for industrial purposes in food, agriculture, medicine and mining. Examples are microorganisms for use in biodetergentes or for production of enzymes for use in detergents, bacteria that synthesize useful products such as indigo, the compound used to dye jeans blue, etc. These microorganisms are subject to stress during the industrial process and their transformation according to the invention will increase their tolerance to salinity, heat, freeze and other stresses.

The salt tolerant transgenic plants or other organisms of the invention are capable of growing under saline conditions, which inhibit the growth of at least 95% of the parent, non-salt tolerant plant or other organisms from which the salt tolerant organisms are derived. Typically, the growth rate of salt tolerant organisms of the invention will be inhibited by less than 50%, preferably less than 30%, and most preferably will have a growth rate which is not significantly inhibited by a growth medium containing water soluble inorganic salts which inhibits growth of at least 95% of the parental, non-salt tolerant plant. Salt concentration under which organisms of the invention are capable of growing are typically between about 20 mM and about 500 mM, often between 40 mM and about 300 mM.

In the case of plants, exemplary water-soluble inorganic salts commonly encountered in saline soils are alkali metal salts, alkaline earth metal salts, and mixtures of alkali metal salts and alkaline earth metal salts. These commonly include sodium sulfate, magnesium sulfate, calcium sulfate, sodium chloride, magnesium chloride, calcium chloride, potassium chloride and the like.

After selecting the transformed cells, the expression of the gene of the invention can be confirmed by standard techniques. Simple detection of mRNA encoded by the inserted DNA can be achieved by well known methods in the art, such as Northern blot hybridization. The inserted sequence can be identified by Southern blot hybridization as well.

In addition, the transformed cells with the salt tolerance phenotype can be selected in vitro by culturing the cells on media containing increased inorganic salt concentrations. For instance, callus tissue can be transferred to standard tissue culture media supplemented with inorganic salts described above, typically sodium chloride. The salt concentration will typically be greater than about 80 mM, preferably about 140 mM, to about 30 mM. The concentration will vary depending upon the sensitivity of the plant being transformed.

Transformed plant cells, which are derived by any of the above transformation techniques can be cultured to regenerate a whole plant, which possesses the transformed genotype and thus display the salt tolerant phenotype. Such regeneration techniques rely on manipulation of certain phytohormones in a tissue culture growth medium, typically relying on a biocide and/or herbicide marker, which has been introduced together with the desired nucleotide sequences.

One of skill will recognize that after the expression vector is stably incorporated in transgenic plants and confirmed to be operable, it can be introduced into other plants by sexual crossing. Any of a number of standard breeding techniques can be used, depending upon the species to be crossed.

The invention will now be illustrated by the following non-limiting examples.

EXAMPLES

Materials and Methods (i) Fungus, yeast strains and culture conditions. *Eurotium herbariorum* was isolated from Dead Sea water (Kis-Papo et al., 2001). It was cultured in GY medium (1% yeast extract, 10% glucose) at 25° C. *Escherichia coli* strain XL/B was used for transformation and plasmid propagation. *E. coli* XL/B was grown in Luria Betani (LB) medium at 37° C. for plasmid manipulation. The *S. cerevisiae* strains used in this study were wild-type YSH6.142-3A (M4Ta leu2-3/112 ura3-1 trp1-1 his3-11/15 ade2-1 can1-100 GAL SUC2 mal0) and YSH444 (AMTa hog1ΔTRP1 mutant) (Albertyn et al., 1994). Yeast cells were grown in a rich medium (YPD) containing 1% yeast extract, 2% peptone, and 2% glucose or in a minimal medium (SD) containing 0.67% yeast nitrogen base and 2% (w/v) glucose supplemented with required amino acids on a rotatory shaker at 30° C. (Sherman, 1991). Agar (1.5%) was added to these media when required.

(ii) DNA and RNA isolation. Mycelia of *E. herbariorum* cultured in GY medium for 2 weeks and harvested by filtration were then soaked in fresh GY medium with 2 M NaCl for various periods of time. Total RNA was prepared from *E. herbariorum* by Total RNA Isolation Kit (Beit Haemek, Israel). DNA from *E. herbariorum* was isolated and purified by a modification of the method of Raeder and Broda (Mcalpin, C. E. 1995). Genomic DNA of yeast was isolated according to a basic protocol (Philippsen et al, 1991).

(iii) DNA and RNA Southern and Northern blot analysis. For Southern Blot analysis, 10 μg of high purity *E. herbariorum* genomic DNA was digested with enzyme EcoRI, HindIII, and BamHI (Biolab) and then transferred to a Hybond N nylon membrane (Amersham). Southern hybridizations (60° C.) were carried out as described by Sambrook et al. (1989). For the probe, an EhHOG-containing DNA fragment (approximately 800 bp) was obtained by PCR amplification with the oligonucleotides: 5'-AAGAAGATTATGAAGC-CTTTCAGC-3' (SEQ ID NO:3) and 5'-CATAATTTTCCAT-GTGTCGACCGG-3' (SEQ ID NO:4) as the primers, and was labeled with [$^{32}$P] dCTP by random primer labeling kit (Beit Haemek, Israel). For Northern blot analysis, the method of hybridization (68° C.) is the same with Southern blots. In general, total RNA was electrophoresed in 1% formaldehyde agarose gels, and blotted onto Hybond N filters (Amersham). The [$^{32}$P] dCTP-labeled 1.1 kb amplified genomic DNA was used as the probe. Hybridization was done in 5× saline-sodium phosphate-EDTA (SSPE), 5, Denhardt's solution, and 0.5% sodium dodecyl sulphate (SDS) for 16 h at 68° C.; filter was washed in 2× saline-sodium citrate (SSC) containing 0.1% SDS at 50° C. (2×30 min), 60° C. (30 min).

(iv) Isolation of EhHOG gene from E. herbariorum. To isolate the HOG gene from E. herbariorum, PCR was performed using genomic DNA as the template and oligonucleotides 5'-ATGGCGGAATTCGTGCGTGCCACGATT-3' (SEQ ID NO:5) and 5'-GGCCGCGAATGCCTGCTGGC-CATCCCC-3' (SEQ ID NO:6) as the primers. PCR amplification was performed using a Peltier thermal cycler (PTC 100, MJ Research, USA) for 35 cycles. Each cycle consisted of 30 s at 94° C., 30 s at 55° C. and 1 min at 72° C. The amplified fragments were subcloned into pGEM-T easy (Promega) and sequenced. To obtain full length HOG cDNA, reverse transcription PCR(RT-PCR) was performed. For RT-PCR, two HOG specific primers 5'-CAAAGCTTATGGCG-GAATTCGTGCGTGCCACGATT-3' (SEQ ID NO:7) and 5'-GGCCGCGAATGCCTGCTGGCCATCCCC-3' (SEQ ID NO:8) were synthesized. First-strand cDNA synthesis was performed in a 20 µl reaction mixture according to cDNA Synthesis system (Promega). The 1 µl sample of first strand cDNA products was then employed as template DNA in PCR for E. herbariorum HOG cDNA. PCR amplification was performed with 50 µl reaction that contained 5 µl 10× buffer, 0.2 mM dNTPs (2 ul 5 mM dNTPs), 1 µl 10 mM HOG specific primer, and 2 units Taq Polymerase (Biotools), using a Peltier thermal cycler for 30 cycles. Each cycle consisted of 30 s at 94° C., 30 s at 55° C., and 1 min at 72° C. The amplified fragments were subcloned into pGEM-T easy (Promega) and sequenced.

(v) Phylogenetic analysis. Phylogenetic trees based on the amino acid sequences alignment of 36 MAPKs were constructed using the neighbor-joining method (Saitou & Nei, 1987) implemented in MAGA2.1 (Kumar et al., 2001). Reliability of the tree topology was evaluated by bootstrap analysis of 1,000 replicates. The resulting estimated amino acid distances were corrected for multiple amino acid substitutions per single site by Poisson correction.

(vi) Functional expression of EhHOG in S. cerevisiae. For expression of EhHOG in S. cerevisiae, 1.1 kb full-length EhHOG cDNA was inserted into HindIII/NotI sites under transcriptional control of the promoter for alcohol dehydrogenase (ADH) in plasmid pADNS (kindly provided by Dr. Y. Kassir, Department of Biology, Technion, Haifa, Israel) resulting in plasmid pADNS-EhHOG. Plasmid pADNS harboring the S. cerevisiae HOG1 coding sequences was obtained by subcloning HindIII-NotI fragments, which was obtained by amplification from S. cerevisiae genomic DNA through the primers 5'-ACAAAGCTTATGACCACTAAC-GAGGAATT-3' (SEQ ID NO. 9) and 5'-CTGGCGGCCGCT-TACTGTTGGAACTCATTAG-3'(SEQ ID NO. 10).

Transformation of yeast cells with pADNS-EhHOG was performed by the lithium acetate/single-stranded carrier DNA/polyethylene glycol methods (Gietz & Woods, 2002).

(vii) Growth Assays. The EhHOG gene was expressed in S. cerevisiae wild strain YSH6.142-3A and mutant YSH444 (AMTa hog1Δ:TRP1), which lacks HOG1. Cultures of strains transformed with pADNS or pADNS-EhGPD were grown in SD-LEU medium and YPD medium in the presence or absence of various concentrations of NaCl, LiCl, and sorbitol. For the growth test, cells were grown at 30° C. for 36 hours; density was adjusted to OD600 at 2. Serial dilution, 1/10, was made at each step. From each dilution, 101 was spotted on different media and incubated at 30° C. for 3-5 days. At various time points, aliquots of the cultures were measured by optical density at 600 nm. For heat stress, cells were grown to $OD_{600}$ 1.8-2. Serial dilutions of ten times were made. Ten microliters of each dilution was spotted on solid YPD plates. Cells on YPD plates were incubated at 42° C. for 1 day and allowed to recover at 28° C. for 36 h and 69 h; for 2-day heat stress, cells recovered at 28° C. for 48 h. Freeze-stress tolerance of cells was determined by measuring viability after the number of freeze-thaw cycles (−30° C. and room temperature). The survival percent was expressed relative to the initial viability prior to freezing. For oxidative stress, cells were grown to $OD_{600}$ 1.0-1.5 in SD medium at 30° C. and then incubated for 1.5 h with increasing concentrations of $H_2O_2$ in SD. The survival percent was expressed relative to the initial viability prior to oxidative stress.

(viii) Northern analysis of mRNA from S. cerevisiae YSH444 strain containing EhHOG. Total RNA was prepared from wild type strain YSH6.142-3A, mutant strain YSH444, and transformant pADNS-EhHOG according to total RNA Isolation Kit (Beit Haemek, Israel). The DNA fragment that encodes the GPD1 of S. cerevisiae was prepared by PCR amplification with oligonucleotides 5'-ATGTCTGCTGCT-GCTGATAG-3' (SEQ ID NO:11) and 5'-AGAGCCTC-GAAAAAAGTGGG-3' (SEQ ID NO:12) as primers and genomic DNA as a template. The DNA fragment was labeled with [$^{32}$-P]dCTP by random primer labeling kit (Beit Haemek, Israel) and used as a GPD1 probe. Northern blot analysis was carried out as described above.

(ix) Assays of intracellular glycerol content in various S. cerevisiae strains. YSH6.142-3A, YSH444 (MATa hog1Δ:: TRP1), and YSH444 with PANDS-EhHOG were cultured at 30° C. in SD media and harvested at the early exponential phase ($OD_{600}$=0.5-0.8). Subsequently, cells were resuspended in a new media with or without 0.4M NaCl. After incubation for 1 hour at 30° C., cells were harvested and washed twice with the same concentration of NaCl. The cell pellet was then suspended in 5 ml distilled water and disrupted by vortexing for 10 min with 5 g glass beads at 4° C. The homogenate was centrifuged for 20 min at 10,000 g at 4° C. The supernatant was immediately heated for 10 min in boiling water to inactivate enzymes connected to the metabolism of glycerol. After centrifugation for 20 min at 10,000 g to remove denatured protein, the supernatant was used to measure the intracellular glycerol concentration. The glycerol content was determined according to the application manual of the glycerol-F kit (Boehringer Mannheim).

(x) Plant Transformation. The putative open reading frame of the EhHOG gene (SEQ ID NO:1) is amplified by PCR. The PCR products are cloned into an pGEM®-T Easy Vectors (Promega) and confirmed by sequence analysis. The EhHOG gene is excised using NcoI and Bst EII and the insert is ligated into the BamHI-SacI restricted pCambia 1301 vector between the CaMV 35S promoter and the nopaline synthase (NOS) terminator sequence of A. tumefaciens. The chimeric construct 35SCaMV-EhHOG-NOS is introduced into A. tumefaciens strain EHA105. Tomato cotyledon explants are infected with A. tumefaciens as described by Gisbert (1997).

Example 1

Isolation and Characterization of the EhHOG from E. herbariorum

Successful amplification of Hog1 homologue in E. herbariorum was achieved with primers (SEQ ID NOs: 3 and 4)

derived from conserved regions of Hog1 from various fungal species available, with flanking regions obtained by chromosome walking (Arnold & Hodgson, 1991). DNA sequence analysis revealed a long open reading frame (ORF) interrupted by eight introns, whose positions were confirmed by sequencing cDNA and genomic DNA clones. This ORF predicted 366-amino acid residues, protein weights of 41.62 KDa, which were highly similar to a kinase from the stress-activated MAPK family. Therefore, the corresponding gene was named EhHOG (*Eurotium herbariorum* HOG). Sequence alignment revealed that the EhHOG protein shows the highest identity to SakA (81% identity, 86% similarity) from *A. nidulans* and also shares a high homology to other MAPKs such as Spc1 (78% identity, 87% similarity) in *Scho. pombe*, Hog1 (66% identity, 72% similarity) in *S. cerevisiae* and Mpkc (60% identity, 74% similarity) in *A. nidulans* (FIG. 1A). A TGY motif, characteristic of hyperosmolarity-activated MAP kinases (Cano and Mahadevan, 1995), was found at amino acids 171-173 (FIG. 1A). Similar motifs have been found in other yeast species (San Jose et al., 1996; Iwaki et al., 1999) and also in MAP kinases from higher eukaryotes, which have been shown to complement *S. cerevisiae* hog1Δ mutants (Han et al., 1994; Rouse et al., 1994; Kumar et al., 1995). This TGY motif indicated to be phosphorylated by MAP kinase (pbs1p) in *S. cerevisiae* (Boguslawski, 1992).

Conserved common docking domain (CD) motif of the MAPK family is present in EhHogp (FIG. 1A). The CD domain contains two acidic amino acids (Asp304, Asp307) (FIG. 1A), which is crucial for docking to a cluster of basic amino acids commonly present in MAPK-docking sites (Tanoue et al., 2000). Asp-304, Asp-307 of EhHogp could serve to establish critical electrostatic interactions with the positively charged amino acids of docking domains of upstream and downstream effectors together with the hydrophobic amino acids Tyr-302 and His-303. This docking motif in MAPKs is commonly used for recognition of their activators, regulators, and substrates. The docking interaction increases the efficiency of all the enzymatic reactions and may help to regulate the specificity of molecular recognition (Enslen & Davis, 2001).

Phylogenetic analysis using representative amino acid sequences from the three major MAPK subgroups indicated that the sequences were clustered primarily by the type of MAPK, forming three major clades: SAPK, ERK, and MAPK3. Within clades ERK and SAPK, several subgroups were clearly identified. On this tree, EhHOG was tightly clustered with HOG subgroup of fungi relatives (*Aspergillus* and yeast) (FIG. 1B). HOG subgroup is characterized by the TGY motif (FIG. 1B), which is found in the sequences of EhHOG (FIG. 1A). HOG subgroup appears more specific in their activation by osmotic stress compared to other signals (Kültz, 1998). In respect to the high-salinity environment of the Dead Sea, EhHOG may have similar specificity to other HOG genes.

Figure 2:
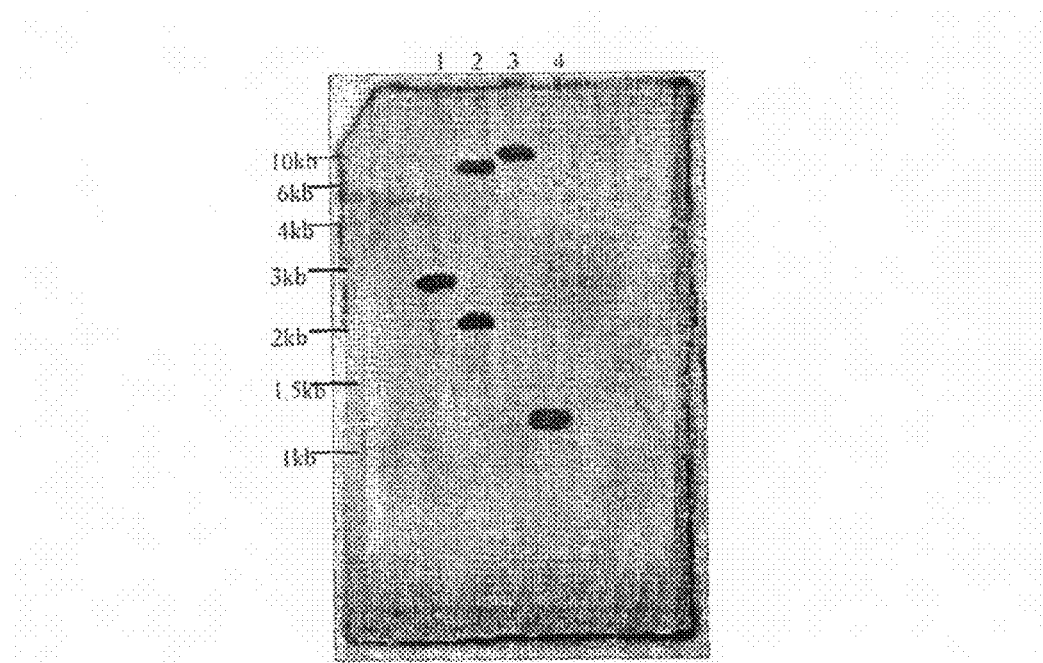
FIG. 2 shows Southern blot analysis of *E. herbariorum* EhHOG gene. The genomic DNA was digested with EcoRI (lane 1); BamHI (lane 2); HindIII (lane 3); AluI (lane 4). A 800 bp PCR fragment was used as a probe.

Southern blot analysis of the genomic DNA was performed in order to estimate the number of EhHOG copies in *E. herbariorum*. The fragments obtained from the genomic DNA digested by the restriction enzymes: EcoRI, HindIII and BamHI, suggested the existence of only one copy of the EhHOG gene in the genome (FIG. 2). The hybridization of the EhHOG probe with the EcoRI digested DNA showed a signal corresponding to one fragment (2.8 kb). One fragment was also detected following hybridization with HindIII (10 kb) and AluI (1.3 kb) digested DNA. Two fragments were detected following hybridization with BamHI digested DNA (9 kb and 2 kb). Since the sequence of EhHOG gene, contained an internal BamHI site the Southern analysis revealed one copy of EhHOG gene in the genome of *E. herbariorum*.

Example 2

Figure 3A:
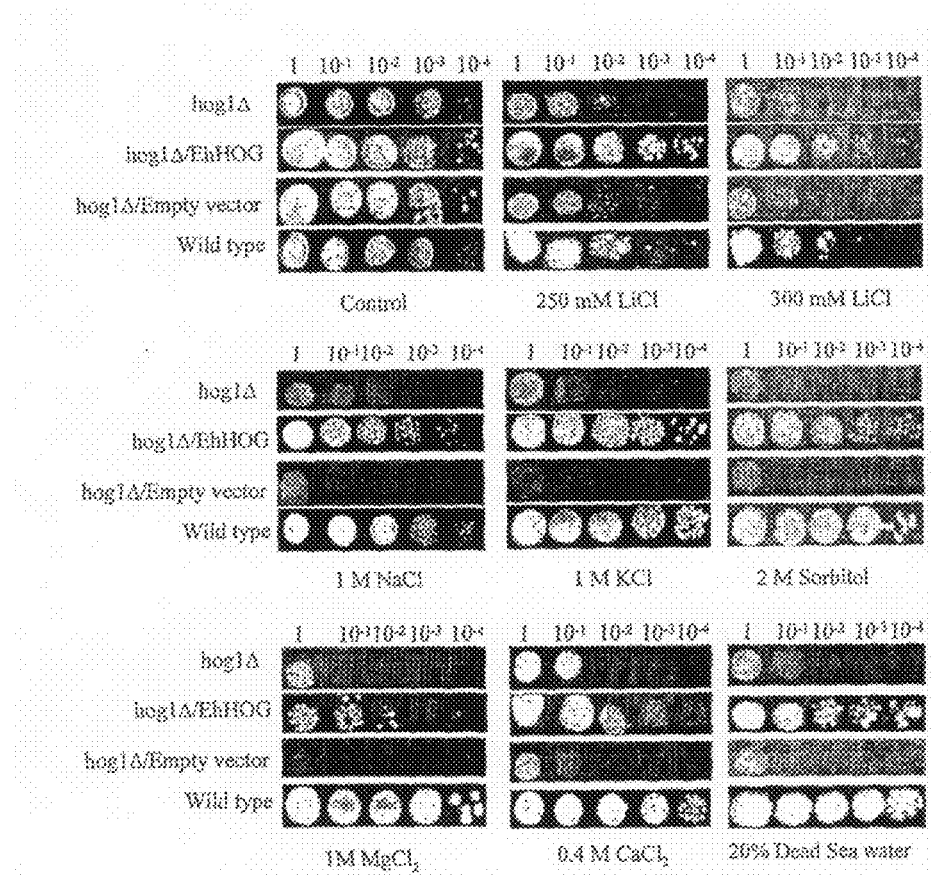
FIG. 3A shows the growth of the *S. cerevisiae* strains: mutant hog1Δ (E), wild type (A), hog1Δ containing EhHOG (E+EhHOG), and hog1Δ containing empty plasmid pADNS (E+pA), in the presence of LiCl, NaCl, KCl, $MgCl_2$, $CaCl_2$, Dead Sea water, and sorbitol. Serial 10-dilutions of saturated cultures (OD600=2) were spotted onto YPD (yeast extract/peptone/dextrose) plates supplemented with LiCl, NaCl, KCl, $MgCl_2$, $CaCl_2$, Dead Sea water, and sorbitol at the concentrations indicated. The plates were then incubated at 30° C.
Figure 3B:
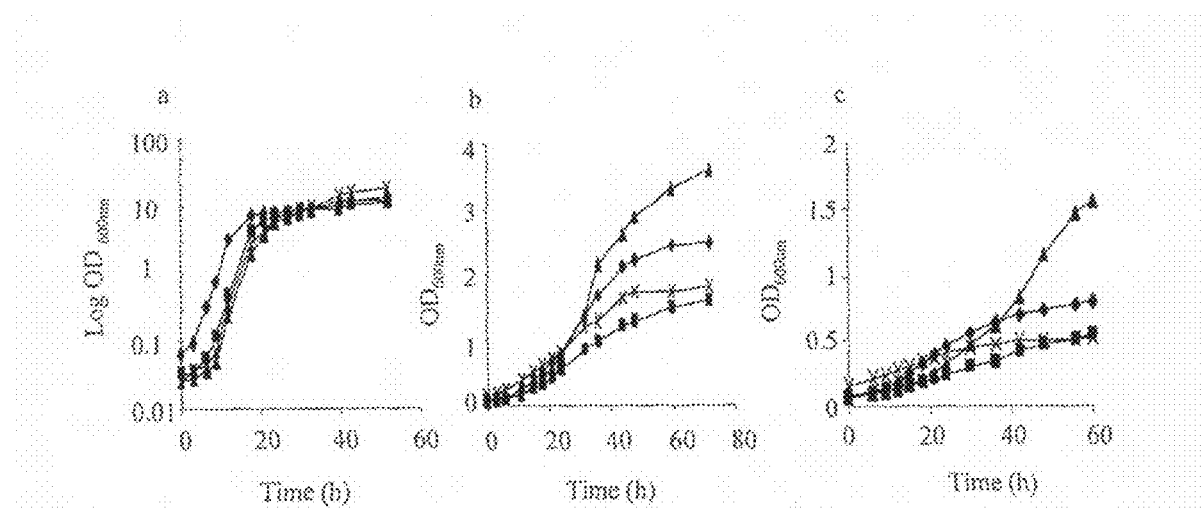
FIG. 3B are graphs showing the growth curves of yeast strains in YPD medium (upper graph), 250 mM LiCl (middle graph), 300 mM LiCl (bottom graph). A, wild type; E, mutant (hog1Δ); E-EhHOG, hog1Δ containing EhHOG; E-PA, empty vector. Growth of cells was estimated by measuring turbidity at 600 nm.

Complementation and Overexpression of a *S. cerevisiae* hog1Δ Mutant by EhHOG in High Salt Stress To determine the functions of EhHOG, complementation of *S. cerevisiae* hog1Δ null mutant (YSH444) was carried out with EhHOG. The salt tolerance of hog1Δ (YSH444 strain) is lower than that of the wild-type strain, because GPDH activity in response to osmotic stress is low when HOG1 (MAP kinase gene) is deleted (Albertyn et al., 1994). If EhHOG could complement the deletion of HOG1 in the *S. cerevisiae* hog1Δ strain, the osmotic tolerance of the transformant strain should be restored compared with the wild type. The coding region of EhHOG was subcloned into a yeast 2μ vector PADNS and recombinant plasmid (pADNS/EhHOG). DNA was transformed into the hog1Δ (YSH444 strain). The transformants were spotted on plates containing 1M NaCl, 1M KCl, 2M Sorbitol, 0.4M $CaCl_2$, 20% Dead Sea water and 300 mM LiCl (FIG. 3A). The mutant hog1Δ could not grow on these plates, but the transformant strain (YSH444 strain containing EhHOG) indicated growth that was comparable to the wild type strain under all these stress conditions and even more tolerant and faster than wild type strain in 300 mM LiCl (FIG. 3A, FIG. 3B). These results indicated that EhHOG has a similar function to the *S. cerevisiae* MAP kinase gene (HOG 1) with respect to salt tolerance in general, whereas $Li^+$ tolerance directed by EhHog1 is clearly higher than that of Hog1 of the wild type.

Figure 4:
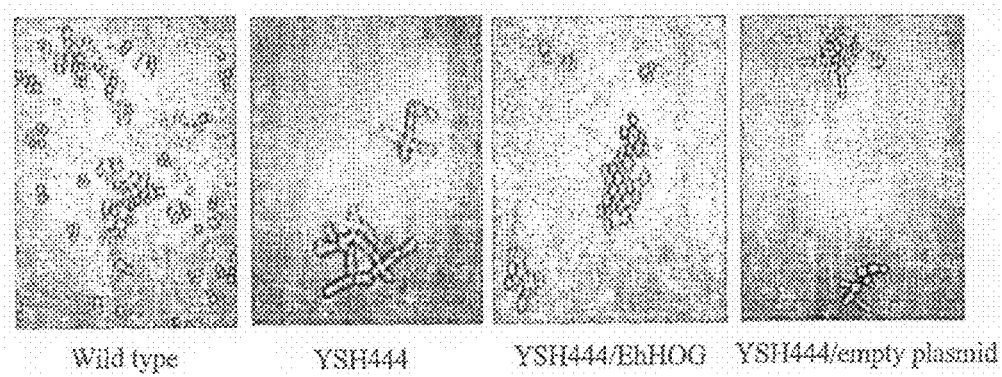
FIG. 4 shows the morphology of *S. cerevisiae* wild type strain (YSH6.142-3A), hog1Δ (YSH444), YSH444 containing EhHOG strain (YSH444/EhHOG) and YSH444/empty plasmid. Cells were grown in the presence of 250 mM LiCl.

*S. cerevisiae* hog1Δ null mutant has an aberrant cell morphology under osmotic stress due to large multinucleated cells with multiple elongated buds (Brewster et al., 1993). However, hog1Δ mutant containing EhHOG showed normal cell shape (FIG. 4). This indicated that the abnormal cell shape of hog1Δ mutants could be rescued by the expression of E1HOG.

Figure 5:
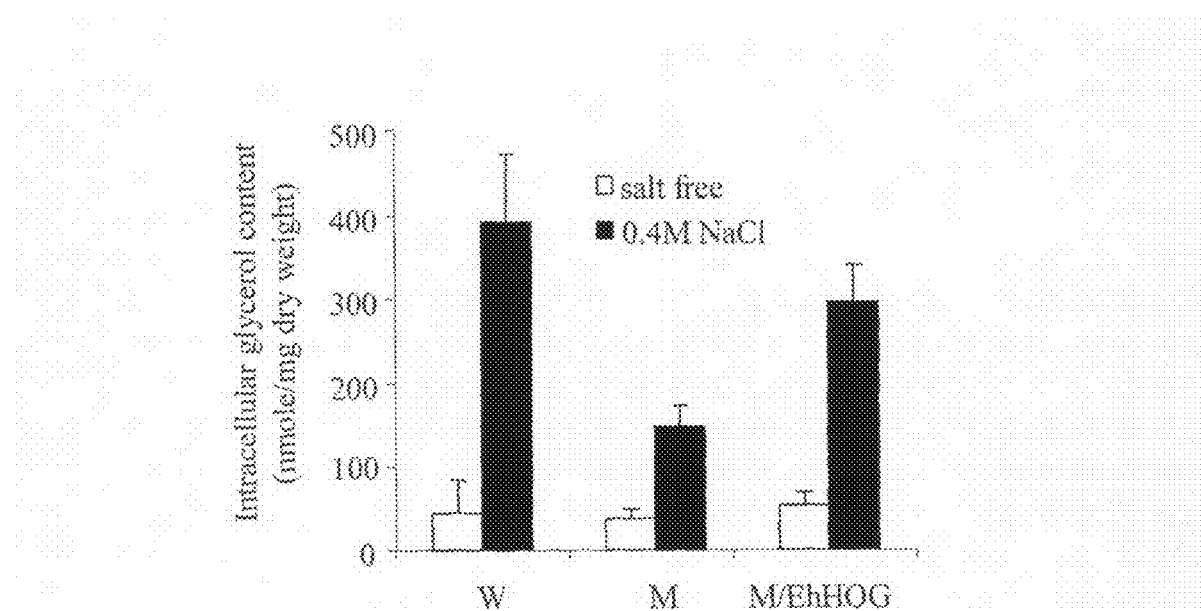
FIG. 5 is a graph showing the change of intracellular glycerol content in *S. cerevisiae* strains wild type (W), hog1Δ mutant (M) and mutant containing EhHOG gene (M/pEhHOG). Cells were grown in SD media and harvested at $OD_{600}$ 0.5-0.8. The cells were resuspended in fresh media with or without 0.4 M NaCl and incubated further for 1 hour at 30° C., and then the intracellular glycerol was measured.

During salt stress, intracellular glycerol content in *S. cerevisiae* hog1Δ mutant increased to a much lower level compared to the wild type strain and the transformant (M/pEhHOG) (FIG. 5).

EhHOG cDNA complemented the hog1Δ null mutation and restored cell growth (FIG. 3A) and morphology (FIG. 4) under salt and osmotic stress conditions. These facts demonstrated the function of MAP kinase (HOG pathway) in the osmosensing signal transduction pathway.

The transformant appeared to have different growth rates on various salt media (FIGS. 3A, 3B) though it restored hog1Δ null mutant growth on diverse salt media. On 250 mM and 300 mM LiCl YPD plates, the transformant grew better than the wild type. This feature is clearly derived from the specific sequence of EhHOG. In addition to its therapeutic effects, $Li^+$ is highly toxic to microorganisms and plants at much lower concentrations compared with that of $Na^+$. $Li^+$ has been widely used as an analogue for $Na^+$ in research on stress with yeasts and plant because of its high sensitivity to all cells and, moreover, low concentrations can be utilized, avoiding screening for osmotolerance (Bohnert et al., 1995). The $Li^+$ concentration in the Dead Sea water is about 100 times higher than that of the normal seas, while the differentials with $Na^+$ and $K^+$ are only about 3 and 20 times, respectively (Mason, 1974; Beyth, 1980). Clearly, $Li^+$ should have exerted much higher selection pressure on any organism living in the Dead Sea in contrast to other ions such as $Na^+$, $K^+$, Ca$^{++}$, Mg$^{++}$. Hence, EhHog is highly likely the outcome of *E. herbariorum's* adaptation to the Dead Sea water with exceptionally high Li$^+$ content.

It has been strongly assumed that there is an equivalent HOG pathway in *E. herbariorum* cells. Moreover, the hog1Δ/EhHOG transformant appeared more salt tolerant than the wild type strain under 250 mM LiCl and 300 mM LiCl (FIG. 3A, FIG. 3B).

In 1 M MgCl$_2$ and 0.4 M CaCl$_2$ YPD media, the wild type strain grew better than the transformant (FIGS. 3A, 3B). On 1 M KCl YPD plate, the transformant grew better in 1 M NaCl. It is possible that Na$^+$ has more toxicity than K$^+$. Uptake of K$^+$ is beneficial for salt tolerance since K$^+$ counteracts the inhibitory effects of Na$^+$ on enzymatic systems (Serrano, 1996).

EhHOG transformant also increased intracellular glycerol content during salt stress (FIG. 5). However, EhHOG did not improve salt tolerance in wild type *S. cerevisiae* (data not shown). These results suggest that EhHOG has similar function to Hog1 in *S. cerevisiae* to regulate GPD1 gene, a second gene involved in glycerol biosynthesis in *S. cerevisiae* (Erikksson et al., 1995).

Example 3

Resistance of EhHOG Against Generalized Stresses

Figure 6:
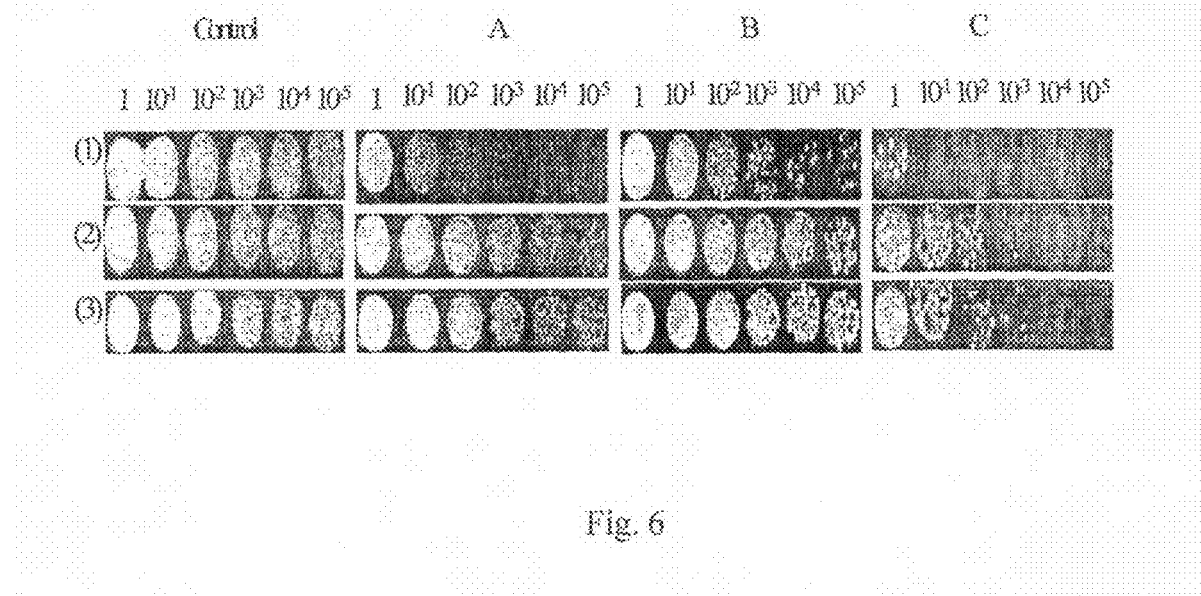
FIG. 6 shows heat stress tolerance of various yeast strains. Yeast cells M (mutant hog1Δ) (1), transformant M/EhHOG (2), and wild type (3) were grown for 24 h in SD (minimal medium) and cell density was adjusted to OD600 at 1.8. Serial dilutions of ten times were made. Ten microliters of each dilution was spotted on solid YPD plates (control). Cells on YPD plates were treated in 42° C. for 1 day and allowed to recover at 28° C. for 36 h (A) and 69 h (B); for 2-day heat stress, cells recovered at 28° C. for 48 h (C).

In addition to having a role in osmoregulation, EhHOG was found to be involved in responses to generalized stresses, such as heat stress and oxidative stress, in *S. cerevisiae* (Winkler et al., 2002), in *Schizosacharomyces pombe* (Degols et al., 1996), and in *Candida albicans* (Alonso-Monge et al., 2003). During heat stress, the growth of hog1Δ strain recovered more slowly than the wild-type strain (FIG. 6). This is consistent with Winkler's result (Winkler et al., 2002). The transformant (hog1Δ/EhHOG) recovered faster than hog1Δ strain, similar to the wild-type strain (FIG. 6). During oxidative stress, hog1Δ strain was more sensitive than the wild-type strain to H$_2$O$_2$, while the transformant (hog1Δ/EhHOG) showed a similar survival rate to the wild-type strain (FIG. 7B). Our study indicated that EhHOG has similar function to Hog1 in *S. cerevisiae* to withstand oxidative stress.

Figure 7A:
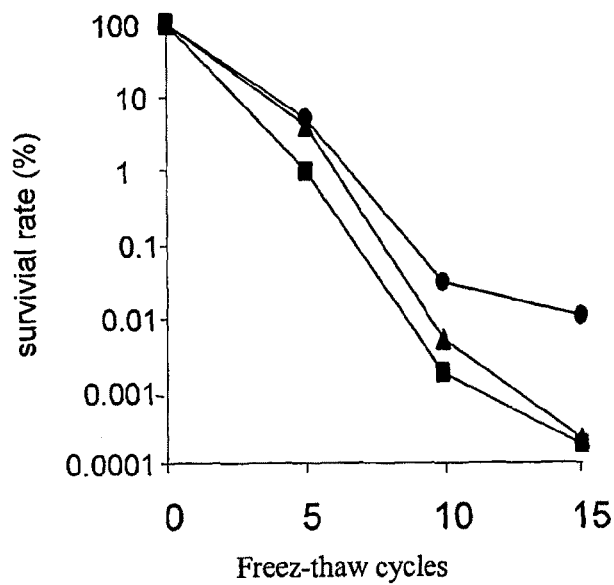
FIGS. 7A-7B show freeze stress and oxidative stress tolerance in various yeast strains. 7A, Freeze stress tolerance of cells was determined by measuring viability after a number of freeze-thaw cycles (−30° C. and room temperature). 7B, Cells were grown to $OD_{600}$ 1.0-1.5 in SD medium at 30° C. and then incubated for 1.5 h with increasing concentrations of $H_2O_2$ in SD. Percent survival was expressed relative to the initial viability prior to freezing or oxidative stress. Results are representative of three independent experiments. Closed triangles—wild type; closed square—M, mutant hog1Δ; closed circle—N/EhHOG.
Figure 7B:
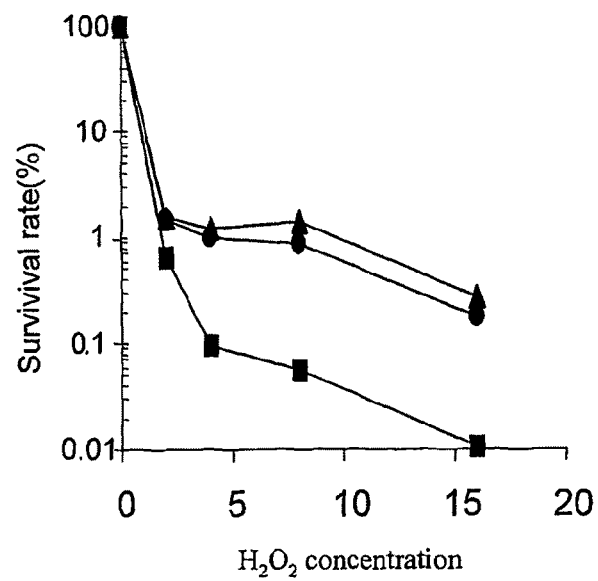

During freeze-thaw stress, the transformant (hog1Δ/EhHOG) survival rate was higher than the wild-type strain, especially after 10 cycles (FIG. 7A). Wild-type strain survival rate decreased rapidly after 10 cycles and reached a similar level to hog1Δ strain in 20 cycles (FIG. 7A). During freezing, cells can be injured by physical factors, such as intracellular ice crystal formation and cellular dehydration. Intracellular ice crystals are believed to rupture the plasma membrane resulting in a release of cellular components into the environment. Glycerol is probably the most widely used cryoprotectant that protects the cells during freezing through minimizing the detrimental effects of increased solute concentration and ice crystal formation. The data presented herein is further supported by Izawa et al. (2004), who recently reported that intracellular glycerol in yeast plays an important role in tolerance to freezing-thawing stress.

During the thawing process, cells suffer oxidative damage to cellular components by reactive oxygen species (Hermes-Lima & Storey, 1993; Park et al., 1998). However, the results provided herein, of the freeze-thaw stress are different from those of oxidative stress. This implies that a higher survival rate in the transformant (hog1Δ/EhHOG) than in the wild-type strain could not be due to high resistance to oxidative stress during freeze-thaw stress. Yeast cells may cope with freeze-thaw stress by synthesis of stress protein (Komatsu et al., 1990) or metabolites such as trehalose and glycerol (Iwahashi et al., 1995; Lewis et al., 1995, 68). Trehalose stabilizes the intracellular water structure and cell membranes under stress conditions (Iwahashi et al., 1995). Freeze-thaw-tolerant yeast strains had higher levels of trehalose (Hino et al., 1990), indicating that trehalose is a possible protectant in freeze-thaw stress. Hence, EhHOG in the transformant possibly promoted the expression of genes involved in glycerol and trehalose synthesis, which produced higher levels of metabolites trehalose and glycerol synthesis in stress survival.

To further eliminate the possibility that the complementation is derived from the copy number of EhHOG or the ADH promoter in the construct (pADNS/EhHOG), Hog1 gene from wild type yeast was isolated and the construct (pADNS/ScHOG1) was made similarly to that of EhHOG (Material & Method). As with EhHOG, *S. cerevisiae* hog1Δ was transformed with pADNS/ScHOG1 and the transformant was tested against all of the stresses as described above. The results show that hog1Δ mutant transformed with wild type Hog1 displayed no significant difference to that of hog1Δ mutant transformed with EhHOG, except for Li$^+$ and freezing-thawing tolerances (data not shown).

The results presented herein demonstrate that EhHOG could perform similarly to other HOGs under a range of stress environments. More importantly, yeast hog1Δ mutant complemented with EhHOG displayed higher tolerance to some types of salts and freezing as well. Evidently, the superior tolerance can be attributed to specific sequences of EhHOG in contrast to other HOGs. These specific sequences are highly likely the products of strong selection pressure from the hypersalinity in the Dead Sea for the last 70,000 years.

Example 4

Genetic Transformation and Molecular Characterization of the EhHOG in Transgenic Tomatoes Cotyledon explants of the tomato cv P-73 are infected with *Agrobacterium tumefaciens* carrying the EhHOG gene in the plasmid. Organogenic calli are selected on kanamycin-containing medium. PCR analysis of plants from independent calli are tested for the presence of the EhHOG gene. PCR positive plants are regenerated from independent calli and PCR negative plant is used as a control. The integration of different numbers of copies is tested by Southern analysis. Northern analysis for the EhHOG gene is done in order to test the presence of mRNA in the transgenic plants.

After molecular characterization, progeny (TG2 and TG3) from a sample of primary transformants (TG1) are obtained and their seeds are used in further experiments. The expression of the EhHOG transgene is detected in these plants. Inheritance of the transgenes is studied in TG2-4 by testing the ability of the explants to grow on media with kanamycin.

To evaluate the level of salt tolerance in vitro in the TG2-4 population, different sources of explants and NaCl concentrations are studied. In the shoot apex test, plant growth is evaluated by measuring rooting capacity, shoot height, number of leaves, and total fresh (FW) and dry (DW) weight of plants after 28 d on culture media with or without NaCl.

To evaluate the physiological response in vivo, three transgenic progeny and control are grown in hydroponic conditions under salt or non-salt conditions. Water content and ion (Na$^+$ and K$^+$) concentrations are measured in roots and leaves after 15 or 30 d of treatments.

REFERENCES

Akhtar, N., Blomberg, A. & Adler, L. (1997) Osmoregulation and protein expression in a pbs2Δ mutant of *Saccharomyces cerevisiae* during adaption to hypersaline stress. *FEBS Lett.* 403, 173-180.

Albertyn, J., Hohmanna, S., Thevelein, J. M. & Prior, B. A. (1994) GPD1, encodes glycerol-3-phosphate dehydrogenase, is essential for growth under osmotic stress in *Saccharomyces cerevisiae*, and its expression is regulated by the high-osmolarity glycerol response pathway. *Mol. Cell. Biol.* 14, 4135-4144.

Alonso-Monge, R., Navarro-Garcia, F., Roman, E., Negredo, A. E., Eisman, B., Nombla, C. & Pla, J. (2003) The hog1 Mitogen-activated protein kinase is essential in the oxidative stress response and Chlamydospore formation in *Candida albicans*. *Eukaryotic Cell* 2, 351-361.

Banuett, F. (1998) Signalling in the yeasts: an informational cascade with links to the filamentous fungi. *Microbiol. Mol. Biol. Rev.* 62, 249-274.

Bansal, P. K. & Mondal, A. K. (2000) Isolation and sequence of the HOG1 homologue from *Debaryomyces hansenii* by complementation of the hog1 delta strain of *Saccharomyces cerevisiae*. Yeast 16, 81-88.

Barcelo P and Lazzeri P A. 'Transformation of cereals by microprojectile bombardment of immature inflorescence and scutellum tissues', in *Methods in Molecular Biology*, H. Jones, ed. 1995, Humana Press Inc.: Totowa, N.J., USA. pp. 113-22.

Becker D, Kemper E, Schell J, Masterson R. New plant binary vectors with selectable markers located proximal to the left T-DNA border. *Plant Mol Biol* 20:1195-1197 (1992).

Becker D, Brettschneider R and Lorz H. Fertile transgenic wheat from microparticle bombardment of scutellar tissue. *Plant Journal* 5(2):299-307 (1994).

Boguslawski, G. (1992) PBS2, a yeast gene encoding a putative protein kinase, interacts with the RAS2 pathway and affects osmotic sensitivity of *Saccharomyces cerevisiae*. *J. Gen. Microbiol.* 138, 2425-2432.

Bohnert, H. J., Nelson, D. E. and Jensenayb, R. G. (1995) Adaptations to Environmental Stresses. *Plant Cell.* 7, 1099-1111.

Brewster, J. L., de Valoir, T., Dwyer, N. D., Winter, E. & Gustin, M. C. (1993) An osmosensing signal transduction pathway in yeast. *Science* 259, 1760-1763.

Buchalo, A. S., Nevo, E., Wasser, S. P., Oren, A & Molitoris, H.-P. (1998) Fungal life in the extremely hypersaline water of the Dead Sea: first records. *Proc. Royal Society London B* 265, 1461-1465.

Cano, E. & Mahadevan L. C. (1995) Paralle signal processing among mammalian MAPKs. *Trends Biochem. Sci.* 20, 117-122.

Cheng M, Fry J E, Pang S, Zhou H, Hironaka C M, Duncan D R, Conner T W and Wan Y, Genetic transformation of wheat mediated by *Agrobacterium tumefaciens*. *Plant Physiology* 115, 971-80 (1997).

Clough S J, Bent A F. Floral dip: a simplified method for *Agrobacterium*-mediated transformation of *Arabidopsis thaliana*. *Plant J* 16: 735-743 (1998).

Degols, G., Shiozaki, K. & Russell, P. (1996) Activation and regulation of the Spc1 stress-activated protein kinase in *Schizosaccharomyces pombe*. *Mol. Cell. Biol.* 16, 2870-2877.

Enslen, H. & Davis, R. J. (2001) Regulation of MAP kinases by docking domains. *Biol. Cell* 93, 5-14.

Erikksson, P., Andre, L., Ansell, R., Blomberg, A. & Adler, L. (1995) Cloning and characterization of GPD2, a second gene encoding an-glycerol 3-phosphate dehydrogenase (NAD+) in *Saccharomyces cerevisiae*, and its comparison with GPD1. *Mol. Microbiol.* 17, 95-107.

Gaxiola R, de Larrinoa I F, Villalba J M, Serrano R. (1992) A novel and conserved salt-induced protein is an important determinant of salt tolerance in yeast. *EMBO J.* 11:3157-3164.

Gelvin S B and Schilperoort R A (Eds), Plant Molecular Biology Manual, 2nd Edition, Kluwer Academic Press, Dordrecht, Netherlands (1994).

Gietz, R. D. & Woods, R. A. (2002) Transformation of yeast by lithium acetate/single-stranded carrier DNA/olyethylene glycol method. In *Methods in Enzymology*, eds. Guthrie, C. & Fink, G. R., 350, 87-92.

Gisbert, C. (1997) Transformacion Genetica en *Lycopersicon*: Introduccion de Genes Relacionados con la Tolerancia a la Salinidad en *L. esculentum* Mill. Cv P-73 y de Genes Maracadores en *L. pennellii* (Corr.) D'Arcy Entrada PE47.

Glaser H U, Thomas D, Gaxiola R, Montrichard F, Surdin-Kerjan Y, Serrano. R. (1993) Salt tolerance and methionine biosynthesis in *Saccharomyces cerevisiae* involve a putative phosphatase gene. *EMBO J.* 12:3105-3110.

Gustin, M. C., Albertyn, J., Alexander, M. & Davenport, K. (1998) MAP kinase pathways in the yeast *Saccharomyces cerevisiae*. *Microbiol. Mol. Biol. Rev.* 62, 1264-1300.

Han, J., Lee, J. D., Bibbs, L. & Ulevitch, R. J. (1994) A MAP kinase targeted by endotoxin and hyperosmolarity in mammalian cells. *Science* 265, 808-811.

Han, K.-H. & Prade, R. A. (2002) Osmotic stress-coupled maintenance of polar growth in *Aspergillus nidulans*. *Mol. Microbiol.* 43, 1065-1078.

Harwood W A, Ross S M, Cilento P, Snape J W. The effect of DNA/gold particle preparation technique, and particle bombardment device, on the transformation of barley (*Hordeum vulgare*). *Euphytica* 111: 67-76 (2000).

Hayashi H., Alia Mustardy L, Deshnium P, Ida M. & Murata N. (1997) Transformation of *Arabidopsis thaliana* with the codA gene for choline oxidase: accumulation of glycine-betaine and enhanced tolerance to salt and cold stress. Plant J 12:133-142.

Hino, A., Mihara, K., Nakashima, K. & Komatsu, Y. (1990) Trehalose levels and survival ratio of freeze-tolerant versus freeze sensitive yeasts. *Appl. Environ. Microbiol.* 56, 1386-1391.

Hirt, H. (1997) Multiple roles of MAP kinases in plant signal transduction. *Trends Plant Sci.* 2, 11-15.

Iwahashi, H., Obuchi, K., Fujii, S. & Komatsu, Y. (1995) The correlative evidence suggesting that trehalose stabilizes membrane structure in the yeast *Saccharomyces cerevisiae*. *Cell. Mol. Biol.* 41, 763-769.

Iwaki, T., Tamai, Y. & Watanabe, Y. (1999) Two putative MAP kinase genes, ZrHOG1 and ZrHOG2, cloned from the salt-tolerant yeast *Zygosaccharomyces rouxii* are functionally homologous to the *Saccharomyces cerevisiae* HOG1 gene. *Microbiol.* 145, 241-248.

Izawa, S., Sato, M., Yokoigawa, K & Inoue, Y (2004) Intracellular glycerol influences resistance to freeze stress in *Saccharomyces cerevisiae*: analysis of a quadruple mutant in glycerol dehydrogenase genes and glycerol-enriched cells. *Appl. Microbiol. Biotechnol.* 66, 108-114.

Kis-Papo, T., Grishkan, I., Oren, A., Wasser, S. P & Nevo, E. (2001) Spatiotemporal diversity of filamentous fungi in the hypersaline Dead Sea. *Mycol. Res.* 105, 749-756.

Kültz, D. (1998) Phylogenetic and functional classification of mitogen- and stress-activated protein kinases. *J. Mol. Evol.* 46, 571-588.

Kumar, S., McLaughlin, M. M., McDonnell, P. C., Lee, J. C., Livi, G. P. & Yong P. R. (1995) Human mitogen-activated protein kinase CSBP1, but not CSBP2, complements a hog1 deletion in yeast. *J. Biol. Chem.* 270, 29043-29046.

Lewis, J. G., Learmonth, R. P. & Watson, K. (1995) Induction of heat, freezing and salt tolerance by heat and salt shock in *Saccharomyces cerevisiae. Microbiology* 141, 687-694.

Mager, H. G. & Varela, J. C. S. (1993) Osmostress response of the yeast *Saccharomyces. Mol. Microbiol.* 10, 253-258.

Marshall, C. J. (1994) MAP kinase kinase kinase, MAP kinase kinase and MAP kinase. *Curr. Opin. Gen. Dev.* 4, 82-89.

Mcalpin, C. E. & Mannarelli, B. (1995) Construction and characterization of a DNA probe for Distinguish Strains of *Aspergillus flavus. Appl Environ. Microbiol.* 61, 1068-1072.

Murguia J R, Belles J M. & Serrano R. (1995) A salt-sensitive 3'(2'),5'-bisphosphate nucleotidase involved in sulfate activation. *Science.* 267:232-234.

Nehra N S, Chibbar R N, Leung N, Caswell K, Mallard C, Steinhauer L, Baga M and Kartha K. (1994) Self-fertile transgenic wheat plants regenerated from isolated scutellar tissues following microprojectile bombardment with two distinct gene constructs. *Plant Journal* 5(2): 285-97.

Nevo E, Oren A and Wasser S P (eds.) (2003) Fungal Life in the Dead Sea (Biodiversity of Cyanoprokaryotes, Algae and Fungi of Israel). Koeltz Scientific Books, Koegnistein, Germany.

Norbeck, J., Pahlman, A. K., Akhtar, N., Blomberg, A. & Adler, L. (1996) Purification and characterization of two isoenzymes of DL-glycerol-3-phosphatase from *Saccharomyces cerevisiae*. Identification of the corresponding GPP1 and GPP2 genes and evidence for osmotic regulation of Gpp2p expression by the osmosensing mitogen-activated protein kinase signal transduction pathway. *J. Biol. Chem.* 271, 13875-13881.

Norbeck, J. & Blomberg, A. (1997) Metabolic and regulatory changes associated with growth of *Saccharomyces cerevisiae* in 1.4 M NaCl. *J. Biol. Chem.* 272, 5544-5554.

Park, J. I., Grant, C. M., Davies, M. J. & Dawes, I. W. (1998) The cytoplasmatic Cu, Zn, superoxide dismutase of *Saccharomyces cerevisiae* is required for resistance to freeze-thaw stress. *J. Biol. Chem.* 36, 22921-22928.

Philippsen, P., Stotz, A. & Scherf, C. (1991) DNA of *Saccharomyces cerevisiae*. In *Methods in Enzymology*, eds. Guthrie, C. and Fink, G. R., 194, 170-172.

Rouse, J., Cohen, P., Trigon, S., Morange, M, Alonso-Llamazares, A., Zamanillo, D., Hunt, T. & Nebreda, A. R. (1994) A novel kinase cascade triggered by stress and heat shock that stimulates MAPKAP kinase-2 and phosphorylation of the small heat shock proteins. *Cell* 78, 1027-1037.

Sambrook J, Fritsch F F and Maniatis T. Molecular Cloning: A Laboratory Manual, 2d edition, Cold Spring Harbor Laboratory Press, Cold Spring Harbor, N.Y. (1989).

San Jose, C., Monge, R. A., Perez-Diaz, R., Pla, J. & Nombela, C. (1996) The mitogen-activated protein kinase homolog HOG1 gene controls glycerol accumulation in the pathogenic fungus *Candida albicans. J. Bacteriol.* 178, 5850-5852.

Serrano, R. (1996) Salt tolerance in plants and microorganisms: toxicity targets and defense responses. *Int. Rev. Cytol.* 165, 1-52.

Sherman, F. (1991) Getting started with yeast. *Methods Enzymol.* 194, 3-21.

Tanoue, T., Adachi, M., Moriguchi, T. & Nishida, E. (2000) A conserved docking motif in MAP kinases common to substrates, activators and regulators. *Nat. Cell. Biol.* 2, 110-116.

Tarczynski, M C., Jensen, R G, & Bohnert, H J. (1993) Stress protection of transgenic tobacco by production of the osmolyte mannitol. *Science* 259:508-510.

Tingay S, McElroy D, Kalla R, Fieg S, Wang M, Thornton S and Brettel R, *Agrobacterium tumefaciens*-mediated barley transformation. *Plant Journal* 11: 1369-76 (1997).

Volcani, B. (1944) The microorganisms of the Dead Sea. In Papers Collected to Commemorate the 70$^{th}$ anniversary of Dr. Chaim Weizmann: 71-85. Daniel Sieff Research Institute, Rehovoth, Israel.

Wan Y and Lemaux P G. Generation of large numbers of independently transformed fertile barley plants. *Plant Physiology* 104: 37-48 (1994).

Weeks J T, Andersen O D and Blechl A E, Rapid production of multiple independent lines of fertile transgenic wheat (*Triticum aestivum* L.). *Plant Physiology* 102(4): 1077-84 (1993).

Winkler, A., Arkind, C., Mattison, C. R., Burkholder, A., Knoche, K. & Ota, I. (2002) Heat stress activates the yeast High-Osmolarity Glycerol Mitogen-Activated protein kinase pathway, and protein tyrosine phosphatases are essential under heat stress. *Eukaryotic Cell* 1, 163-173.

The invention claimed is:

1. An isolated nucleic acid, comprising a DNA having a nucleotide sequence selected from the group consisting of SEQ ID NO: 1 and isolated DNA having a nucleotide sequence differing from SEQ. ID NO: 1 in codon sequence due to the degeneracy of the genetic code.

2. The isolated nucleic acid according to claim 1, comprising a DNA consisting of the nucleotide sequence of SEQ ID NO: 1, said DNA consisting of the coding sequence of EhHOG, encoding for the EhHOG protein of *Eurotium herbariorum* of SEQ ID NO: 2.

3. A chimeric construct capable of expression in host cells, comprising: (a) a DNA sequence of SEQ ID NO: 1 coding for the EhHOG protein of SEQ ID NO: 2, and (b) DNA sequences enabling expression of the EhHOG protein in host cells.

4. A chimeric construct according to claim 3, wherein the DNA sequences enabling expression of the EhHOG protein includes a promoter operably linked to the DNA sequence of SEQ ID NO: 1.

5. A chimeric construct according to claim 4, wherein the promoter is selected from the group consisting of a constitutive promoter, a tissue-specific promoter and a stress-induced promoter.

6. A recombinant vector comprising the nucleic acid according to claim 2.

7. An expression vector comprising the chimeric construct according to claim 3.

8. A host cell transformed with the nucleic acid according to claim 2, wherein said host cell is a yeast cell or a plant cell.

9. A transgenic plant generated from a plant cell according to claim 8.

10. A transgenic plant transformed with the DNA of SEQ ID NO: 1 that encodes the protein EhHOG consisting of the amino acid sequence as shown in SEQ ID NO: 2, said DNA being operably linked to DNA sequences enabling expression of the EhHOG protein in plant cells and subsequent improvement of tolerance of the plant to abiotic stress.

11. A transgenic plant according to claim 10, comprising a recombinant expression vector comprising a plant promoter operably linked to the DNA of SEQ ID NO: 1.

12. A transgenic plant which contains in its cells a chimeric construct according to claim 3 such that the plant exhibits tolerance to abiotic stress.

13. A transgenic plant according to claim 10, wherein said abiotic stress is osmotic, heat, freeze, dehydration, oxidative or high salinity stress.

14. A transgenic plant according to claim 13, wherein said plant is selected from the group consisting of tomato, rice, wheat, barley, corn, oats, beans including soybean, and peas.

15. A biologically pure culture of a microorganism transformed with an isolated nucleic acid comprising the DNA of SEQ ID NO: 1 that encodes the protein EhHOG consisting of the amino acid sequence as shown in SEQ ID NO: 2, said DNA being operably linked to DNA sequences enabling expression of the EhHOG protein in the microorganism cells and subsequent improvement of tolerance of the microorganism to abiotic stress.

16. A biologically pure culture according to claim 15, wherein said microorganism is yeast or bacteria.

\* \* \* \* \*

SEQUENCE LISTING

```
<160> NUMBER OF SEQ ID NOS: 16

<210> SEQ ID NO 1
<211> LENGTH: 1101
<212> TYPE: DNA
<213> ORGANISM: Artificial Sequence
<220> FEATURE:
<223> OTHER INFORMATION: synthetic

<400> SEQUENCE: 1
atggcggaat  tcgtgcgtgc  cacgattttc  ggcaccacct  tcgaaatcac  cagccggtac    60
acggagctgc  aaccggtggg  aatgggtgcc  tttggtcttg  tttgtgccgc  aagagatcaa   120
ttgaccggag  cgcccgtcgc  cgtcaagaag  attatgaagc  ctttcagcac  acccgtcctg   180
tccaagagaa  catatcgcga  actgaagctc  ttgaagcatt  tgggccatga  gaacattatc   240
tgcctgagcg  acatttttcat  ttccccgctc  gaggacattt  attccgtcac  cgaactcctg   300
ggcaccgacc  ttcatagact  cttaacttct  cgaccattag  agaagcaatt  catccaatat   360
```

```
ttcctttacc agattttgcg gggtctaaaa tatgtccact cagccggtgt cgtgcatcgt      420
gatctcaaac cgagcaatat cctgatcaac gaaaactgtg acctgaagat tgcggtttt       480 ggtttggccc gggttcaaga cccgcagatg actggttacg tgtcgacgag atattatcgc      540
gccccggaga ttatgcttac atggcaaaag tatgatgtgg aggtcgacat ctggagtgca      600
gggtgtatct ttgctgagat gctcgacggg aagccgctgt tccctggcaa ggaccatgtc      660
aaccaattct ccattatcac cgaattactg ggtacgccgc cagacgacgt gatcgagacc      720
atttgcagtg aaaacacatt gcgattcgtc aagtcgcttc ctaagcggga acggcaacca      780
ttgactagca ggttcaagaa tgcggaccct gaggcggtgg accttctgga acgaatgctg      840
gtctttgacc ccaagaagcg aatccgcgcc ggtgaggctc tggcgcacga ataccttgct      900
ccataccacg atcccaccga cgagcccgag gcgcaagaga aattcgactg gtcgttcaac      960
gatgcggatc tgccggtgga cacctggagg atcatgatgt actcggagat cctcgacttc     1020
cacaacatcg accaaagcga ggatgccggg caagtccttg tcgaaggcgt cggggatggc     1080
cagcaggcat tcgcggccta g                                                1101
```

<210> SEQ ID NO 2
<211> LENGTH: 366
<212> TYPE: PRT
<213> ORGANISM: Artificial Sequence
<220> FEATURE:
<223> OTHER INFORMATION: Synthetic

<400> SEQUENCE: 2

```
Met Ala Glu Phe Val Arg Ala Thr Ile Phe Gly Thr Thr Phe Glu Ile
1               5                   10                  15

Thr Ser Arg Tyr Thr Glu Leu Gln Pro Val Gly Met Gly Ala Phe Gly
            20                  25                  30

Leu Val Cys Ala Ala Arg Asp Gln Leu Thr Gly Ala Pro Val Ala Val
        35                  40                  45

Lys Lys Ile Met Lys Pro Phe Ser Thr Pro Val Leu Ser Lys Arg Thr
    50                  55                  60

Tyr Arg Glu Leu Lys Leu Leu Lys His Leu Gly His Glu Asn Ile Ile
65                  70                  75                  80

Cys Leu Ser Asp Ile Phe Ile Ser Pro Leu Glu Asp Ile Tyr Ser Val
                85                  90                  95

Thr Glu Leu Leu Gly Thr Asp Leu His Arg Leu Leu Thr Ser Arg Pro
            100                 105                 110

Leu Glu Lys Gln Phe Ile Gln Tyr Phe Leu Tyr Gln Ile Leu Arg Gly
        115                 120                 125

Leu Lys Tyr Val His Ser Ala Gly Val Val His Arg Asp Leu Lys Pro
    130                 135                 140

Ser Asn Ile Leu Ile Asn Glu Asn Cys Asp Leu Lys Ile Cys Gly Phe
145                 150                 155                 160

Gly Leu Ala Arg Val Gln Asp Pro Gln Met Thr Gly Tyr Val Ser Thr
                165                 170                 175

Arg Tyr Tyr Arg Ala Pro Glu Ile Met Leu Thr Trp Gln Lys Tyr Asp
            180                 185                 190

Val Glu Val Asp Ile Trp Ser Ala Gly Cys Ile Phe Ala Glu Met Leu
        195                 200                 205

Asp Gly Lys Pro Leu Phe Pro Gly Lys Asp His Val Asn Gln Phe Ser
    210                 215                 220

Ile Ile Thr Glu Leu Leu Gly Thr Pro Pro Asp Asp Val Ile Glu Thr
```

```
                225                 230                 235                 240
Ile Cys Ser Glu Asn Thr Leu Arg Phe Val Lys Ser Leu Pro Lys Arg
                245                 250                 255
Glu Arg Gln Pro Leu Thr Ser Arg Phe Lys Asn Ala Asp Pro Glu Ala
            260                 265                 270
Val Asp Leu Leu Glu Arg Met Leu Val Phe Asp Pro Lys Lys Arg Ile
        275                 280                 285
Arg Ala Gly Glu Ala Leu Ala His Glu Tyr Leu Ala Pro Tyr His Asp
    290                 295                 300
Pro Thr Asp Glu Pro Glu Ala Gln Glu Lys Phe Asp Trp Ser Phe Asn
305                 310                 315                 320
Asp Ala Asp Leu Pro Val Asp Thr Trp Arg Ile Met Met Tyr Ser Glu
                325                 330                 335
Ile Leu Asp Phe His Asn Ile Asp Gln Ser Glu Asp Ala Gly Gln Val
                340                 345                 350
Leu Val Glu Gly Val Gly Asp Gly Gln Gln Ala Phe Ala Ala
            355                 360                 365
```

<210> SEQ ID NO 3
<211> LENGTH: 24
<212> TYPE: DNA
<213> ORGANISM: Artificial sequence
<220> FEATURE:
<223> OTHER INFORMATION: Synthetic

<400> SEQUENCE: 3
aagaagatta tgaagccttt cagc                                              24

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
cataattttc catgtgtcga ccgg                                              24

<210> SEQ ID NO 5
<211> LENGTH: 27
<212> TYPE: DNA
<213> ORGANISM: Artificial Sequence
<220> FEATURE:
<223> OTHER INFORMATION: Synthetic

<400> SEQUENCE: 5
atggcggaat tcgtgcgtgc cacgatt                                           27

<210> SEQ ID NO 6
<211> LENGTH: 27
<212> TYPE: DNA
<213> ORGANISM: Artificial Sequence
<220> FEATURE:
<223> OTHER INFORMATION: Synthetic

<400> SEQUENCE: 6
ggccgcgaat gcctgctggc catcccc                                           27

<210> SEQ ID NO 7
<211> LENGTH: 35
<212> TYPE: DNA
<213> ORGANISM: Artificial Sequence
<220> FEATURE:

<223> OTHER INFORMATION: Synthetic

<400> SEQUENCE: 7
caaagcttat ggcggaattc gtgcgtgcca cgatt                                    35

<210> SEQ ID NO 8
<211> LENGTH: 27
<212> TYPE: DNA
<213> ORGANISM: Artificial Sequence
<220> FEATURE:
<223> OTHER INFORMATION: Synthetic

<400> SEQUENCE: 8
ggccgcgaat gcctgctggc catcccc                                            27

<210> SEQ ID NO 9
<211> LENGTH: 29
<212> TYPE: DNA
<213> ORGANISM: Artificial Sequence
<220> FEATURE:
<223> OTHER INFORMATION: Synthetic

<400> SEQUENCE: 9
acaaagctta tgaccactaa cgaggaatt                                          29

<210> SEQ ID NO 10
<211> LENGTH: 31
<212> TYPE: DNA
<213> ORGANISM: Artificial Sequence
<220> FEATURE:
<223> OTHER INFORMATION: Synthetic

<400> SEQUENCE: 10
ctggcggccg cttactgttg gaactcatta g                                       31

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
atgtctgctg ctgctgatag                                                    20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
agagcctcga aaaaagtggg                                                    20

<210> SEQ ID NO 13
<211> LENGTH: 349
<212> TYPE: PRT
<213> ORGANISM: Saccharomyces pombe

<400> SEQUENCE: 13

Met Ala Glu Phe Ile Arg Thr Gln Ile Phe Gly Thr Cys Phe Glu Ile
1               5                   10                  15

Thr Thr Arg Tyr Ser Asp Leu Gln Pro Ile Gly Met Gly Ala Phe Gly
            20                  25                  30

```
Leu Val Cys Ser Ala Lys Asp Gln Leu Thr Gly Met Asn Val Ala Val
             35                  40                  45

Lys Lys Ile Met Lys Pro Phe Ser Thr Pro Val Leu Ala Lys Arg Thr
 50                  55                  60

Tyr Arg Glu Leu Lys Leu Leu Lys His Leu Arg His Glu Asn Ile Ile
 65                  70                  75                  80

Ser Leu Ser Asp Ile Phe Ile Ser Pro Phe Glu Asp Ile Tyr Phe Val
                 85                  90                  95

Thr Glu Leu Leu Gly Thr Asp Leu His Arg Leu Leu Thr Ser Arg Pro
                100                 105                 110

Leu Glu Thr Gln Phe Ile Gln Tyr Phe Leu Tyr Gln Ile Leu Arg Gly
            115                 120                 125

Leu Lys Phe Val His Ser Ala Gly Val Ile His Arg Asp Leu Lys Pro
        130                 135                 140

Ser Asn Ile Leu Ile Asn Glu Asn Cys Asp Leu Lys Ile Cys Asp Phe
145                 150                 155                 160

Gly Leu Ala Arg Ile Gln Asp Pro Gln Met Thr Gly Tyr Val Ser Thr
                165                 170                 175

Arg Tyr Tyr Arg Ala Pro Glu Ile Met Leu Thr Trp Gln Lys Tyr Asn
                180                 185                 190

Val Glu Val Asp Ile Trp Ser Ala Gly Cys Ile Phe Ala Glu Met Ile
            195                 200                 205

Glu Gly Lys Pro Leu Phe Pro Gly Arg Asp His Val Asn Gln Phe Ser
210                 215                 220

Ile Ile Thr Glu Leu Leu Gly Thr Pro Pro Met Glu Val Ile Glu Thr
225                 230                 235                 240

Ile Cys Ser Lys Asn Thr Leu Arg Phe Val Gln Ser Leu Pro Gln Lys
                245                 250                 255

Glu Lys Val Pro Phe Ala Glu Lys Phe Lys Asn Ala Asp Pro Asp Ala
            260                 265                 270

Ile Asp Leu Leu Glu Lys Met Leu Val Phe Asp Pro Arg Lys Arg Ile
        275                 280                 285

Ser Ala Ala Asp Ala Leu Ala His Asn Tyr Leu Ala Pro Tyr His Asp
290                 295                 300

Pro Thr Asp Glu Pro Val Ala Asp Glu Val Phe Asp Trp Ser Phe Gln
305                 310                 315                 320

Asp Asn Asp Leu Pro Val Glu Thr Trp Lys Val Met Met Tyr Ser Glu
                325                 330                 335

Val Leu Ser Phe His Asn Met Asp Asn Glu Leu Gln Ser
            340                 345

<210> SEQ ID NO 14
<211> LENGTH: 435
<212> TYPE: PRT
<213> ORGANISM: Saccharomyces cerevisiae

<400> SEQUENCE: 14

Met Thr Thr Asn Glu Glu Phe Ile Gly Thr Gln Ile Phe Gly Thr Val
 1               5                  10                  15

Phe Glu Ile Thr Asn Arg Tyr Asn Asp Leu Asn Pro Val Gly Met Gly
             20                  25                  30

Ala Phe Gly Leu Val Cys Ser Ala Thr Asp Thr Leu Thr Ser Gln Pro
         35                  40                  45

Val Ala Ile Lys Lys Ile Met Lys Pro Phe Ser Thr Ala Val Leu Ala
     50                  55                  60
```

```
Lys Arg Thr Tyr Arg Glu Leu Lys Leu Leu Lys His Leu Arg His Glu
 65                  70                  75                  80

Asn Leu Ile Cys Leu Gln Asp Ile Phe Leu Ser Pro Leu Glu Asp Ile
                 85                  90                  95

Tyr Phe Val Thr Glu Leu Gln Gly Thr Asp Leu His Arg Leu Leu Gln
            100                 105                 110

Thr Arg Pro Leu Glu Lys Gln Phe Val Gln Tyr Phe Leu Tyr Gln Ile
        115                 120                 125

Leu Arg Gly Leu Lys Tyr Val His Ser Ala Gly Val Ile His Arg Asp
130                 135                 140

Leu Lys Pro Ser Asn Ile Leu Ile Asn Glu Asn Cys Asp Leu Lys Ile
145                 150                 155                 160

Cys Asp Phe Gly Leu Ala Arg Ile Gln Asp Pro Gln Met Thr Gly Tyr
                165                 170                 175

Val Ser Thr Arg Tyr Tyr Arg Ala Pro Glu Ile Met Leu Thr Trp Gln
            180                 185                 190

Lys Tyr Asp Val Glu Val Asp Ile Trp Ser Ala Gly Cys Ile Phe Ala
        195                 200                 205

Glu Met Ile Glu Gly Lys Pro Leu Phe Pro Gly Lys Asp His Val His
210                 215                 220

Gln Phe Ser Ile Ile Thr Asp Leu Leu Gly Ser Pro Pro Lys Asp Val
225                 230                 235                 240

Ile Asn Thr Ile Cys Ser Glu Asn Thr Leu Lys Phe Val Thr Ser Leu
                245                 250                 255

Pro His Arg Asp Pro Ile Pro Phe Ser Glu Arg Phe Lys Thr Val Glu
            260                 265                 270

Pro Asp Ala Val Asp Leu Leu Glu Lys Met Leu Val Phe Asp Pro Lys
        275                 280                 285

Lys Arg Ile Thr Ala Ala Asp Ala Leu Ala His Pro Tyr Ser Ala Pro
290                 295                 300

Tyr His Asp Pro Thr Asp Glu Pro Val Ala Asp Ala Lys Phe Asp Trp
305                 310                 315                 320

His Phe Asn Asp Ala Asp Leu Pro Val Asp Thr Trp Arg Val Met Met
                325                 330                 335

Tyr Ser Glu Ile Leu Asp Phe His Lys Ile Gly Gly Ser Asp Gly Gln
            340                 345                 350

Ile Asp Ile Ser Ala Thr Phe Asp Asp Gln Val Ala Ala Ala Thr Ala
        355                 360                 365

Ala Ala Ala Gln Ala Gln Ala Gln Ala Gln Ala Gln Val Gln Leu Asn
370                 375                 380

Met Ala Ala His Ser His Asn Gly Ala Gly Thr Thr Gly Asn Asp His
385                 390                 395                 400

Ser Asp Ile Ala Gly Gly Asn Lys Val Ser Asp His Val Ala Ala Asn
                405                 410                 415

Asp Thr Ile Thr Asp Tyr Gly Asn Gln Ala Ile Gln Tyr Ala Asn Glu
            420                 425                 430

Phe Gln Gln
        435

<210> SEQ ID NO 15
<211> LENGTH: 379
<212> TYPE: PRT
<213> ORGANISM: Aspergillus nidulans

<400> SEQUENCE: 15
```

```
Met Ala Glu Phe Val Arg Ala Gln Ile Phe Gly Thr Thr Phe Glu Ile
1               5                   10                  15

Thr Ser Arg Tyr Thr Asp Leu Gln Pro Val Gly Met Gly Ala Phe Gly
            20                  25                  30

Leu Val Cys Ser Ala Arg Asp Gln Leu Thr Ala Gln Pro Val Ala Val
        35                  40                  45

Lys Lys Ile Met Lys Pro Phe Ser Thr Pro Val Leu Ser Lys Arg Thr
50                  55                  60

Tyr Arg Glu Leu Lys Leu Leu Lys His Leu Arg His Glu Asn Ile Ile
65                  70                  75                  80

Ser Leu Ser Asp Ile Phe Ile Ser Pro Leu Glu Asp Ile Tyr Phe Val
                85                  90                  95

Thr Glu Leu Leu Gly Thr Asp Leu His Arg Leu Ile Ser Ser Arg Pro
                100                 105                 110

Leu Glu Lys Gln Phe Ile Gln Tyr Phe Leu Tyr Gln Ile Met Arg Gly
            115                 120                 125

Leu Lys Tyr Val His Ser Ala Gly Val Val His Arg Asp Leu Lys Pro
130                 135                 140

Ser Asn Ile Leu Ile Asn Glu Asn Cys Asp Leu Lys Ile Cys Asp Phe
145                 150                 155                 160

Gly Leu Ala Arg Ile Gln Asp Pro Gln Met Thr Gly Tyr Val Ser Thr
                165                 170                 175

Arg Tyr Tyr Arg Ala Pro Glu Ile Met Leu Thr Trp Gln Lys Tyr Asp
                180                 185                 190

Ala Lys Val Asp Val Trp Ser Ala Ala Cys Ile Phe Ala Glu Met Leu
            195                 200                 205

Leu Gly Ala Pro Leu Phe Pro Gly Lys Asp His Val Asn Gln Phe Ser
210                 215                 220

Ile Ile Thr Glu Leu Leu Gly Thr Pro Pro Asp Asp Val Ile Gln Thr
225                 230                 235                 240

Ile Cys Ser Glu Asn Thr Leu Arg Phe Val Lys Ser Leu Pro Lys Arg
                245                 250                 255

Glu Pro Gln Asp Leu Ala Lys Leu Pro Lys Phe Leu Ala Leu Val His
                260                 265                 270

Pro Asp Lys Lys Pro Glu Glu Asp Glu Asp Tyr Lys Asn Thr Ile Asn
            275                 280                 285

Leu Leu Lys Ala Met Leu Val Tyr Asn Pro Lys Asp Arg Ile Ser Ala
290                 295                 300

Glu Ala Ala Leu Ala Ala Pro Tyr Leu Ala Pro Tyr His Asp Glu Thr
305                 310                 315                 320

Asp Glu Pro Val Ala Glu Glu Lys Phe Asp Trp Ser Phe Asn Asp Ala
                325                 330                 335

Asp Leu Pro Val Asp Thr Trp Lys Ile Met Met Tyr Ser Glu Ile Leu
                340                 345                 350

Asp Phe His Asn Ile Asp Gln Gly Gly Asp Ile Asn Pro Ala Leu Val
            355                 360                 365

Glu Gly Ala Gly Leu Asn Gln Gln Gly Phe Gln
370                 375

<210> SEQ ID NO 16
<211> LENGTH: 347
<212> TYPE: PRT
<213> ORGANISM: Aspergillus nidulans

<400> SEQUENCE: 16
```

-continued

```
Met Ala Glu Phe Ile Arg Ser Asp Ile Leu Gly Thr Thr Phe Glu Thr
 1               5                  10                 15
Thr Ser Arg Tyr Ala Asn Leu Gln Pro Val Gly Leu Gly Thr Ala Gly
             20                  25                 30
Val Val Cys Ser Ala Tyr Asp Leu Ile Ser Glu Gln Val Val Ala Ile
         35                  40                  45
Lys Lys Met Met Lys Pro Phe His Ser Thr Ser Val Ala Lys Arg Thr
     50                  55                  60
Tyr Arg Glu Val Lys Leu Leu Arg His Leu Arg His Asp Asn Leu Ile
 65                  70                  75                 80
Asn Met Ser Asp Ile Phe Ile Ser Pro Leu Glu Asp Val Tyr Leu Val
                 85                  90                 95
Thr Glu Leu Leu Gly Thr Asp Leu His Arg Leu Leu Asn Gly Lys Pro
            100                 105                110
Leu Glu Ser Lys Phe Ala Gln Tyr Phe Thr Tyr Gln Ile Leu Arg Gly
            115                 120                 125
Leu Lys Tyr Ile His Ser Ala Gly Val Ile His Arg Asp Leu Lys Pro
        130                 135                 140
Gly Asn Leu Leu Ile Asn Glu Asn Cys Asp Leu Lys Ile Cys Asp Phe
145                 150                 155                 160
Gly Leu Ala Arg Val Gln Glu Pro Gln Met Thr Gly Tyr Val Ser Thr
                165                 170                 175
Arg Tyr Tyr Arg Ala Pro Glu Ile Met Leu Thr Trp Gln Arg Tyr Gly
            180                 185                 190
Ser Lys Val Asp Leu Trp Ser Val Gly Cys Ile Leu Ala Glu Met Leu
        195                 200                 205
Leu Gly Arg Pro Leu Phe Pro Gly Thr Asp His Ile Asn Gln Phe Trp
210                 215                 220
Leu Ile Thr Asp Leu Leu Gly Asn Pro Pro Asp Glu Val Ile Asp Arg
225                 230                 235                 240
Ile Thr Thr Asn Asn Val Arg Asn Pro Ala Pro Asp Leu Gln Pro Ser
                245                 250                 255
Asn His Leu Glu Pro Ala Asn Gly Asn Arg Arg Ile Asp Ser Ser Gly
            260                 265                 270
Ala Leu Asn Leu Leu Asp Asn Leu Leu Val Phe Asp Pro Asp Arg Arg
        275                 280                 285
Ile Ser Ala Glu Gln Gly Leu Met His Pro Trp Met Ala Pro Tyr His
        290                 295                 300
Asp Pro Thr Asp Glu Pro Val Ala Thr Glu Gln Phe Asp Trp Ser Phe
305                 310                 315                 320
Asn Asp Ala Asp Leu Pro Leu Asp Thr Trp Lys Ile Met Met Tyr Val
                325                 330                 335
His His Cys Ser Asp Val Val Ser Phe Thr Leu
            340                 345
```